US008455002B2

(12) United States Patent
Shaw et al.

(10) Patent No.: US 8,455,002 B2
(45) Date of Patent: Jun. 4, 2013

(54) STABLE CORTICOSTEROID NANOPARTICULATE FORMULATIONS AND METHODS FOR THE MAKING AND USE THEREOF

(75) Inventors: Kenneth Shaw, Weston, CT (US); Mingbao Zhang, Millwood, NY (US)

(73) Assignee: Marinus Pharmaceuticals, Branford, CT (US)

( * ) Notice: Subject to any disclaimer, the term of this patent is extended or adjusted under 35 U.S.C. 154(b) by 127 days.

(21) Appl. No.: 12/777,920

(22) Filed: May 11, 2010

(65) Prior Publication Data
US 2011/0008453 A1 Jan. 13, 2011

Related U.S. Application Data

(63) Continuation-in-part of application No. 11/998,362, filed on Nov. 28, 2007, now abandoned.

(60) Provisional application No. 61/215,873, filed on May 11, 2009, provisional application No. 60/861,616, filed on Nov. 28, 2006.

(51) Int. Cl.
| | |
|---|---|
| *A61K 9/14* | (2006.01) |
| *A61K 47/14* | (2006.01) |
| *A61K 47/28* | (2006.01) |
| *C07J 71/00* | (2006.01) |
| *A61K 8/63* | (2006.01) |

(52) U.S. Cl.
CPC ............. *A61K 47/14* (2013.01); *A61K 9/145* (2013.01); *A61K 8/63* (2013.01); *C07J 71/00* (2013.01); *Y10S 977/906* (2013.01)
USPC ............ 424/489; 424/501; 514/172; 977/906

(58) Field of Classification Search
None
See application file for complete search history.

(56) References Cited

U.S. PATENT DOCUMENTS

| | | | |
|---|---|---|---|
| 2,671,750 A | 3/1954 | Macek et al. | |
| 4,540,602 A | 9/1985 | Motoyama et al. | |
| 4,783,484 A | 11/1988 | Violante et al. | |
| 4,826,689 A | 5/1989 | Violanto et al. | |
| 4,997,454 A | 3/1991 | Violante et al. | |
| 5,145,684 A | 9/1992 | Liversidge et al. | |
| 5,209,746 A | 5/1993 | Balaban et al. | |
| 5,213,808 A | 5/1993 | Bar-Shalom et al. | |
| 5,221,278 A | 6/1993 | Linkwitz et al. | |
| 5,260,068 A | 11/1993 | Chen | |
| 5,260,069 A | 11/1993 | Chen | |
| 5,298,262 A | 3/1994 | Na et al. | |
| 5,299,131 A | 3/1994 | Haas et al. | |
| 5,308,348 A | 5/1994 | Balaban et al. | |
| 5,312,390 A | 5/1994 | Wong | |
| 5,318,588 A | 6/1994 | Horzewski et al. | |
| 5,340,590 A | 8/1994 | Wong et al. | |
| 5,346,702 A | 9/1994 | Na et al. | |
| 5,352,459 A | 10/1994 | Hollister et al. | |
| 5,356,467 A * | 10/1994 | Oshlack et al. ............ | 106/161.1 |
| 5,391,381 A | 2/1995 | Wong et al. | |
| 5,399,363 A | 3/1995 | Liversidge et al. | |
| 5,429,824 A | 7/1995 | June | |
| 5,445,829 A | 8/1995 | Paradissis et al. | |
| 5,456,679 A | 10/1995 | Balaban et al. | |
| 5,470,583 A | 11/1995 | Na et al. | |
| 5,472,708 A | 12/1995 | Chen | |
| 5,494,683 A | 2/1996 | Liversidge et al. | |
| 5,508,040 A | 4/1996 | Chen | |
| 5,510,118 A | 4/1996 | Bosch et al. | |
| 5,518,187 A | 5/1996 | Bruno et al. | |
| 5,534,270 A | 7/1996 | De Castro | |
| 5,543,133 A | 8/1996 | Swanson et al. | |
| 5,560,932 A | 10/1996 | Bagchi et al. | |
| 5,573,783 A | 11/1996 | Desieno et al. | |
| 5,629,277 A * | 5/1997 | Plishka ........................ | 510/202 |
| 5,662,883 A | 9/1997 | Bagchi et al. | |
| 5,665,331 A | 9/1997 | Bagchi et al. | |
| 5,672,360 A | 9/1997 | Sackler et al. | |
| 5,718,388 A | 2/1998 | Czekai et al. | |
| 5,741,522 A | 4/1998 | Violante et al. | |
| 5,776,496 A | 7/1998 | Violante et al. | |
| 5,840,329 A | 11/1998 | Bai | |
| 5,862,999 A | 1/1999 | Czekai et al. | |
| 5,980,508 A | 11/1999 | Cardamone et al. | |
| 6,039,979 A | 3/2000 | Gendrot et al. | |
| 6,161,536 A * | 12/2000 | Redmon et al. .......... | 128/200.14 |
| 6,214,379 B1 | 4/2001 | Hermelin | |

(Continued)

FOREIGN PATENT DOCUMENTS

| | | |
|---|---|---|
| EP | 0169618 | 11/1993 |
| EP | 0498824 | 1/1994 |

(Continued)

OTHER PUBLICATIONS

MG Soni, SL Taylor, NA Greenberg, GA Burdock. "Evaluation of the health aspects of methyl paraben: a review of the published literature." Food and Chemical Toxicology, vol. 40, 2002, pp. 1335-1373.*
Joh Sham, Y Zhang, WH Finlay, WH Roa, R Lobenberg. "Formulation and characterization of spray-dried powders containing nanoparticles for aerosol delivery to the lung." International Journal of Pharmaceutics, vol. 269, 2004, pp. 457-467.*
A Valotis, K Neukam, O Elert, P Hogger. "Human Receptor Kinetics, Tissue Binding Affinity, and Stability of Mometasone Furoate." Journal of Pharmaceutical Sciences, vol. 93, No. 5, May 2004, pp. 1337-1350.*
H. Steffen BT Gattefosse No. 81 pp. 45-53 (1988).

(Continued)

*Primary Examiner* — Frederick Krass
*Assistant Examiner* — Isaac Shomer
(74) *Attorney, Agent, or Firm* — Davidson, Davidson & Kappel, LLC

(57) ABSTRACT

Disclosed are stable corticosteroid nanoparticulate formulations, methods of making and therapeutic uses thereof.

28 Claims, 6 Drawing Sheets

U.S. PATENT DOCUMENTS

Figure 1:
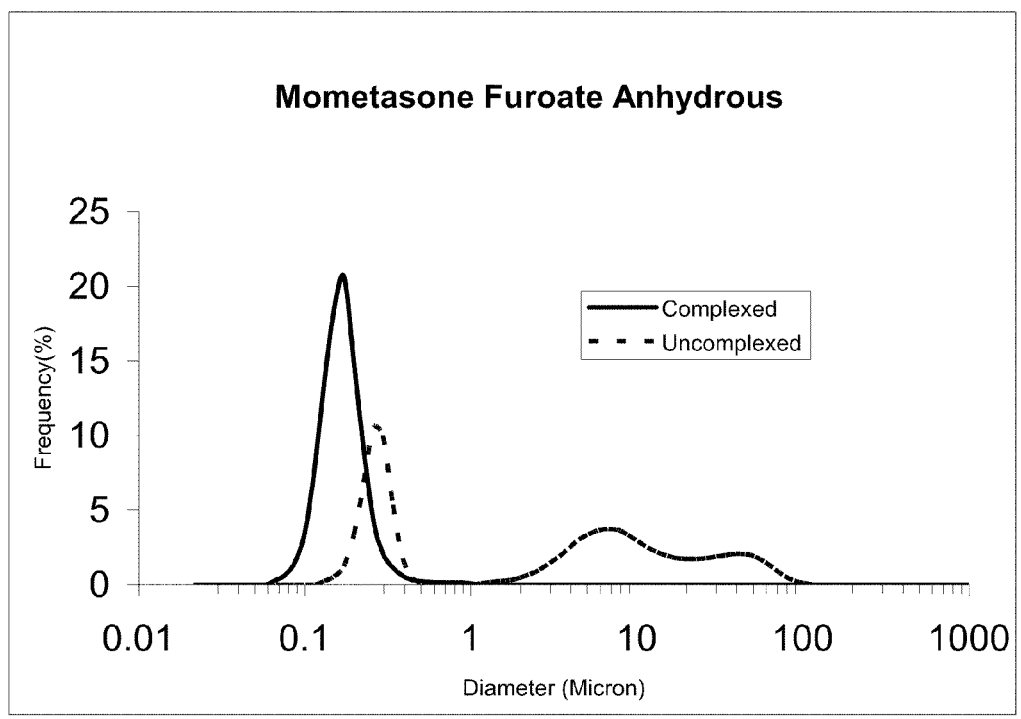

| | | | |
|---|---|---|---|
| 6,228,398 B1 | 5/2001 | Devane et al. | |
| 6,248,363 B1 | 6/2001 | Patel et al. | |
| 6,264,922 B1 * | 7/2001 | Wood et al. | 424/45 |
| 6,267,989 B1 | 7/2001 | Liversidge et al. | |
| 6,316,029 B1 | 11/2001 | Jain et al. | |
| 6,375,986 B1 | 4/2002 | Ryde et al. | |
| 6,423,746 B1 | 7/2002 | Yarbrough et al. | |
| 6,428,814 B1 | 8/2002 | Bosch et al. | |
| 6,432,381 B2 | 8/2002 | Liversidge et al. | |
| 6,514,518 B2 | 2/2003 | Monkhouse et al. | |
| 6,569,463 B2 | 5/2003 | Patel et al. | |
| 6,592,903 B2 | 7/2003 | Ryde et al. | |
| 6,607,751 B1 | 8/2003 | Odidi et al. | |
| 6,627,223 B2 | 9/2003 | Percel et al. | |
| 6,682,759 B2 | 1/2004 | Lim et al. | |
| 6,689,378 B1 | 2/2004 | Sun et al. | |
| 6,730,325 B2 | 5/2004 | Devane et al. | |
| 6,793,936 B2 | 9/2004 | Devane et al. | |
| 6,902,742 B2 | 6/2005 | Davane et al. | |
| 6,908,626 B2 | 6/2005 | Cooper et al. | |
| 6,923,988 B2 | 8/2005 | Patel et al. | |
| 6,969,529 B2 | 11/2005 | Bosch et al. | |
| 6,976,647 B2 | 12/2005 | Reed et al. | |
| 7,078,057 B2 | 7/2006 | Kerkhof | |
| 7,198,795 B2 | 4/2007 | Cooper et al. | |
| 7,858,609 B2 | 12/2010 | Shaw | |
| 8,022,054 B2 | 9/2011 | Shaw | |
| 2002/0012675 A1 | 1/2002 | Jain et al. | |
| 2002/0150616 A1 | 10/2002 | Vandecruys | |
| 2003/0054042 A1 | 3/2003 | Liversidge et al. | |
| 2003/0129242 A1 * | 7/2003 | Bosch et al. | 424/489 |
| 2003/0215502 A1 | 11/2003 | Pruss et al. | |
| 2004/0067251 A1 | 4/2004 | Johnston et al. | |
| 2004/0105889 A1 | 6/2004 | Ryde et al. | |
| 2004/0214746 A1 | 10/2004 | Bosch et al. | |
| 2004/0224020 A1 | 11/2004 | Schoenhard | |
| 2004/0258757 A1 | 12/2004 | Bosch et al. | |
| 2005/0031691 A1 | 2/2005 | McGurk et al. | |
| 2005/0118268 A1 | 6/2005 | Percel et al. | |
| 2005/0181050 A1 | 8/2005 | Hirsh et al. | |
| 2005/0226927 A1 | 10/2005 | Han et al. | |
| 2005/0232890 A1 * | 10/2005 | Hoath et al. | 424/70.14 |
| 2006/0003005 A1 | 1/2006 | Cao et al. | |
| 2006/0216353 A1 | 9/2006 | Liversidge et al. | |
| 2007/0148252 A1 | 6/2007 | Shaw et al. | |
| 2009/0004262 A1 | 1/2009 | Shaw et al. | |
| 2011/0236487 A1 | 9/2011 | Shaw | |
| 2012/0052098 A1 | 3/2012 | Shaw | |

FOREIGN PATENT DOCUMENTS

| | | |
|---|---|---|
| EP | 0499299 | 8/2000 |
| EP | 0580690 | 9/2000 |
| WO | WO 9526715 | 10/1995 |
| WO | WO 9857648 | 12/1998 |
| WO | WO 0145677 | 6/2001 |

OTHER PUBLICATIONS

Monaghan et al. "Initial human experience with ganaxolene, a neuroeactive steroid with antiepileptic activity." Epilepsia, 1997, vol. 38, issue 9, pp. 1026-1031.

Delmar Learning's Pharmacy Technician Certification Exam Review, Edition 2, 2003, 584 pages by Patricia K. Anthony.

Fabian, Can. J. Chem. 82: 50-69 (2004).

* cited by examiner

STABLE CORTICOSTEROID NANOPARTICULATE FORMULATIONS AND METHODS FOR THE MAKING AND USE THEREOF

This application claims the benefit under 35 U.S.C. §119 (e) of U.S. Provisional Patent Application No. 61/215,873, filed May 11, 2009, the disclosure of which is hereby incorporated by reference in its entirety. This application is also a continuation-in-part of U.S. patent application Ser. No. 11/998,362, filed Nov. 28, 2007, which claims the benefit under 35 U.S.C. §119(e) of U.S. Provisional Patent Application No. 60/861,616, filed Nov. 28, 2006, the disclosures of which are hereby incorporated by reference in their entirety.

BACKGROUND OF THE INVENTION

Background Regarding Corticosteroids

Depending on the mode of administration, corticosteroids can be used to treat, for example, corticosteroid-responsive diseases of the upper and lower airway passages and lungs, such as seasonal (e.g., hay fever) or perennial rhinitis, which are characterized by seasonal or perennial sneezing, rhinorrhea, nasal congestion, pruritis and eye itching, redness and tearing, and nonallergic (vasomotor) rhinitis (i.e., eosinophilic nonallergic rhinitis which is found in patients with negative skin tests and those who have numerous eosinophils in their nasal secretions). The term "allergic rhinitis" as used herein includes any allergic reaction of the nasal mucosa.

Corticosteroids (Glucocorticosteroids) have been shown to be effective for the maintenance treatment of asthma as a prophylactic therapy, for the management of the nasal symptoms of seasonal and perennial allergic and nonallergic rhinitis in adults and pediatric patients, and for the relief of the signs and symptoms of seasonal allergic conjunctivitis.

Glucocorticosteroid formulations have been designed for intranasal delivery and also as formulations designed for inhaled delivery to the lung via a suspension of particles in a propellant or by direct inhalation of particles in the solid form.

Intranasal delivery of corticosteroids is usually accomplished by actuation of a metered dose device containing a suspension of colloidal/microcrystalline particles. These particles are generally above 1 micron in size. Several issues in formulation intranasal corticosteroids involve homogeneity, irritation, taste, stability, preservatives as well as limited types of ingredients and amounts approved for intranasal use as one does not want irritation or toxicity to the mucosal lining in the nose or to affect normal ciliary action in the nose or impair any sense of smell or taste.

Delivery of drugs to the nasal mucosa can also be accomplished with aqueous, propellant-based, or dry powder formulations. However, absorption of poorly soluble drugs can be problematic because of mucociliary clearance which transports deposited particles from the nasal mucosa to the throat where they are swallowed. Complete clearance generally occurs within about 15-20 minutes. Thus, poorly soluble drugs which do not dissolve within this time frame are unavailable for either local or systemic activity.

Other issues of current marketed glucocorticosteroid formulations involve systemic exposure to some corticosteroids which may lead to unwanted steroidal side-effects. Also, the onset of action is not immediate and may take several days to achieve full efficacy. This is especially important in allergic rhinitis where quick relief from allergic symptoms is desired. If these issues can be resolved, this type of treatment would be safer and more efficacious.

A representative example of a corticosteroid currently in use is mometasone furoate monohydrate: Mometasone furoate is described and claimed in U.S. Pat. Nos. 5,837,699; 6,127,353; and 6,723,713 (to Schering Corporation), the disclosures of which are hereby incorporated by reference. The compound has anti-inflammatory activity and is particularly useful for the treatment of respiratory disorders, particularly upper airway diseases.

Depending on the mode of administration, mometasone furoate can be used to treat, for example, corticosteroid-responsive diseases of the upper and lower airway passages and lungs, such as seasonal (e.g., hay fever) or perennial rhinitis, which are characterized by seasonal or perennial sneezing, rhinorrhea, nasal congestion, pruritis and eye itching, redness and tearing, and nonallergic (vasomotor) rhinitis (i.e., eosinophilic nonallergic rhinitis which is found in patients with negative skin tests and those who have numerous eosinophils in their nasal secretions). The term "allergic rhinitis" as used herein includes any allergic reaction of the nasal mucosa.

In addition, the mometasone furoate compositions described herein can be used to treat asthma, including any asthmatic condition marked by recurrent attacks of paroxysmal dyspnea (i.e., reversible obstructive airway passage disease) with wheezing due to spasmodic contraction of the bronchi. Asthmatic conditions which may be treated or prevented in accordance with this invention include allergic asthma and bronchial allergy characterized by manifestations in sensitized persons provoked by a variety of factors including exercise, especially vigorous exercise (exercise induced bronchospasm), irritant particles (e.g., pollen, dust, cotton, dander, etc.), as well as mild to moderate asthma, chronic asthma, severe chronic asthma, severe and unstable asthma, nocturnal Mometasone furoate is also approved for topical dermatologic use to treat inflammatory and/or pruritic manifestations of corticosteroid-responsive dermatoses. Thus, like other topical corticosteroids, mometasone furoate has anti-inflammatory, antipruritic, and vasoconstrictive properties.

Mometasone furoate is marketed as NASONEX® Nasal Spray (Shering Corporation) and mometasone furoate monohydrate is the active component in this commercial product. NASONEX® Nasal Spray, 50 mcg is a metered-dose, manual pump spray unit containing an aqueous suspension of mometasone furoate monohydrate equivalent to 0.05% w/w mometasone furoate calculated on the anhydrous basis; in an aqueous medium containing glycerin, microcrystalline cellulose and carboxymethylcellulose sodium, sodium citrate, 0.25% w/w phenylethyl alcohol, citric acid, benzalkonium chloride, and polysorbate 80. The pH is between 4.3 and 4.9. Adverse reactions from the current marketed form of mometasone furoate monohydrate include headache, viral infection, pharyngitis, eptistaxis/blood-tinged mucus, coughing, upper respiratory tract infection, dysmenorrheal, musculoskeletal pain, sinusitis and vomiting.

After initial priming (10 actuations), each actuation of the pump delivers a metered spray containing 100 mg of suspension containing mometasone furoate monohydrate equivalent to 50 mcg of mometasone furoate calculated on the anhydrous basis. NASONEX is a corticosteroid and the precise mechanism of corticosteroid action on allergic rhinitis is not known. Corticosteroids have been shown to have a wide range of effects on multiple cell types (e.g., mast cells, eosinophils, neutrophils, macrophages, and lymphocytes) and mediators (e.g., histamine, eicosanoids, leukotrienes, and cytokines)

involved in inflammation. Intranasal corticosteroids may cause a reduction in growth velocity when administered to pediatric patients.

There are several disadvantages with conventional nasal dosage forms of mometasone furoate monohydrate, including the use of benzalkonium chloride as a preservative. The presence of benzalkonium chloride limits the use of these formulations because some patients are allergic to benzalkonium chloride and other patients find the smell to be unpleasant. The onset of action in allergic rhinitis can take several days. Any formulation which can create a faster onset of action, better efficacy while not increasing systemic exposure would be highly desirable. The current marketed product does not contain salt (Nasonex®) and application of intransal corticosteroids in some isotonic media is preferred to increase tolerability.

Inhaled delivery of corticosteroid particles must be controlled for the aerodynamic particles size as targeted delivery to the lung must be optimized so the patient in need does not swallow or exhale a significant portion of the dose. Very small particles (100-200 nm) might be expected to be significantly exhaled so small inhaled corticosteroid formulations must be adjusted to have a redispersible agglomerate of smaller particles with the effective particle size of the agglomerate in the 1-4 micron range.

B. Background Regarding Nanoparticulate Corticosteroid Compositions

Several Patents and applications exist regarding the preparation of corticosteroid sub-micron (nanoparticulate) formulations. The anticipation of small particle corticosteroids compositions is that they may offer the following advantages: (1) the composition may be formulated in a dried form which readily redisperses; (2) the composition may offer a potential decrease in the frequency of dosing; (3) smaller doses of drug may be required to obtain the same pharmacological effect as compared to conventional microcrystalline or soluble forms of corticosteroids; (6) the nanoparticulate compositions may not require organic solvents or pH extremes.

Nanoparticulate compositions for cocorticosteroids are described, for example, in U.S. Pat. No. 6,264,922 for "Aerosols Containing Nanoparticulate Dispersions," U.S. Pat. No. 5,747,001 for "Aerosols Containing Beclomethasone Nanoparticle Dispersions;" U.S. 20040208833 A1 to Hovey et al., for "Novel fluticasone formulations, U.S. Pat. No. 7,459,146v for "Stabilized Aerosol Dispersions", US 20040057905 A1 to Wood et al., for "Nanoparticulate beclomethasone dipropionate compositions," US 20040141925 to Bosch et al., for "Novel triamcinolone compositions," US 20030129242 to Bosch et al., for "Sterile filtered nanoparticulate formulations of budesonide and beclomethasone having tyloxapol as a surface stabilizer", US 20070178051 to Pruitt et al., for "Sterilized Nanoparticulate Glucocorticosteroid Formulations", WO/2007/064912 to Hovey et al. for " Mometasone Compositions and Methods of Making and Using the Same".

One way to provide for a small "nano" particle drug formulation is to form a submicron particle liquid formulation, e.g., nanosuspension. When dealing with nanosuspensions, the less water soluble and more lipophilic the drug, the more difficult it is to obtain a stable small particle "nanosuspension" in polar solvents like water. Particle growth (Otswald Ripening) and aggregation must be minimized in nanoparticulate compositions if the benefit of small particle formulations is to be realized.

Preparation of nanosuspensions is known in the art. The preparation of small particle pharmaceutical compositions (effective particle size (D50) of less than 500 nm) have been described since 1988 (H. Steffen BT Gattefosse No. 81, 1988 pp. 45-53; U.S. Pat. No. 4,540,602 (Motoyama, et al.); and U.S. Pat. No. 5,145,684 (Liversidge, et al.)). These submicron (nanoparticulate) compositions all describe using non-crosslinked excipients associated with the surface of the small particle to stabilize the composition from significant particle size growth and/or agglomeration. Generally, surface stabilizers fall into two categories: non-ionic (also called steric stabilizers or modifiers) and ionic stabilizers. The most common non-ionic stabilizers are excipients which are contained in classes known as binders, fillers, surfactants and wetting agents. Limited examples of non-ionic surface stabilizers are hydroxypropylmethyl cellulose, polyvinylpyrrolidone, Plasdone, polyvinyl alcohol, Pluronics, Tweens and Polyethyleneglycols (PEGs). A subset of surface stabilizers commonly used is ionic in nature. These ionic surface stabilizers tend to fall into the class of excipients which are typically used as surfactants and wetting agents. Ionic stabilizers used in the prior art are typically organic molecules bearing an ionic bond such that the molecule is essentially fully charged in the formulation. The two most described ionic surface stabilizers are the long chain sulfonic acid salts sodium lauryl sulfate and dioctyl sodium sulfosuccinate (DOSS). Broad ranges for all surface stabilizers have been claimed in U.S. Pat. No. 5,145,684 (the '684 patent) ranging from 0.1% to 90% by weight of the composition. Typically, one adds 20%-150% (wt % of drug) of a nonionic surface stabilizer and 0.2%-5% of an ionic surface stabilizer (wt % of drug) to achieve maximal particle size stabilization from these surface stabilizers. Since 1988, many papers and patents have published relating to nanoparticulate compositions and various ways to optimize the method of manufacture, use and stability of such compositions. These surface stabilizers are diffusion controlled and the prior art teaches that one typically needs at least 15% of the steric stabilizer (w/w) based on drug to prevent particle size growth upon storage. The patent literature generally claims amounts of surface stabilizers in relation to the drug in suspension or the percent weight of the composition. Wide ranges are generally claimed for these stabilizers and little or no attention has been paid to the amount of surface stabilizers needed to stabilize nanoparticulate drugs at low or high concentrations. Corticosteroid suspensions are unusual in standard nanoparticle stabilization for several reasons. They are quite lipophilic and water insoluble creating a large potential for the drug particles to agglomerate in a polar environment such as water or physiological fluids. Corticosteroids are extremely potent drugs so the amount delivered is small and stabilization of drugs at low concentration is not generally addressed in the prior art. The amount and type of approved additives for intranasal and inhaled compositions is much more limiting than those allowed for oral administration. We have found that as one dilutes corticosteroids suspensions the amount of steric surface stabilizers (e.g. HPMC) must be increased relative to the amount of drug in the suspension to maintain stabilization of particle size upon storage. Surprisingly, once the composition is cured with a complexing agent, it can be diluted without addition of more complexing agent while the attributes of a complexed particle is maintained. This is an unexpected finding as stabilizers of small particles are considered reversible and diffusion controlled.

It would be advantageous to provide nanoparticulate formulations for corticosteroids which provide enhanced stability (storage and in physiological media), physical and chemical properties and can provide enhanced absorption in the nose or lungs to achieve an optimal balance between pharmacodynamic and side effect profiles in mammals, and dosage forms containing the same, as well as methods of making nanoparticulate drug formulations and their use in the treatment of various disorders.

DETAILED SUMMARY OF THE INVENTION

Described herein are nanoparticulate corticosteroid compositions, methods for manufacturing, methods for treatment therewith, as well as, treatment strategies and pharmacokinetic strategies using the nanoparticulate formulations.

Also described herein are intranasal and inhalation nanoparticulate corticosteroid formulations, methods for manufacturing, methods for treatment therewith, as well as, treatment strategies and pharmacokinetic strategies using the nanoparticulate formulations.

The inventors have prepared stable submicron corticosteroids drug particles with particularly advantageous pharmaceutical properties. Stable drug particles described herein comprise a complex of drug and a complexing agent. Additional factors that affect stability and particle size are described herein.

Certain Definitions

As used herein, the terms "comprising," "including", "containing" and "such as" are used in their open, non-limiting sense.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. Thus compositions slightly outside the cited ranges are also encompassed by the scope of the present claims.

For purposes of the invention, the term "drug" means any therapeutically active corticosteroid for inhaled or intranasal use. "Bioavailability" refers to the degree to which a drug becomes available at the site(s) of action after administration. By way of illustration, the bioavailability of a drug formulation refers to the percentage of the weight of drug dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which drug is absorbed into the general circulation when the pharmaceutical composition is taken orally as compared to intravenous injection. The degree and timing in which an active agent becomes available to the target site(s) after administration is determined by many factors, including the dosage form and various properties, e.g., solubility and dissolution rate of the drug.

A "blood serum concentration" or "blood plasma concentration" or "serum or plasma concentration or level", typically measured in mg, μg, or ng of a drug per ml, dl, or l of serum or plasma absorbed into the bloodstream after administration. As used herein, measurable plasma concentrations are typically measured in ng/ml or μg/ml. It is understood that the plasma concentration of a drug may vary significantly between subjects, due to variability with respect to metabolism and/or possible interactions with other therapeutic agents. In accordance with one aspect of the present invention, the blood plasma concentration of drug may vary from subject to subject. Likewise, values such as measured concentration of the active agent in the plasma at the point of maximum concentration ($C_{max}$) or time to reach maximum plasma concentration ($T_{max}$), or total area under the plasma concentration time curve ($AUC_{(0-\infty)}$) may vary from subject to subject.

"$AUC_{(0-\tau)}$" or "exposure or bioavailability" is the area under the curve of a graph of the concentration of the active agent (typically plasma concentration) vs. time (τ), measured from time 0 to τ. $AUC_{(0-\tau)}$ is also used to define the exposure to the drug over a defined period of time. Due to variability, the amount necessary to constitute "a therapeutically effective amount" of drug may vary from subject to subject.

"Carrier materials" include any commonly used excipients in pharmaceutics and should be selected on the basis of compatibility with drug and the release profile properties of the desired dosage form.

The term "curing" means treating the drug (either before, during or after particle size reduction) with a complexing agent under suitable conditions to obtain a size stabilized drug product. In certain embodiments, a measurement of stability can be via the comparison of the particle size (e.g., D50) of the uncomplexed drug versus the complexed drug in physiological media or the degree of particle size change in physiological media versus water.

The term "curing time" means a sufficient time until an endpoint is reached such that the properties of the (complexed) drug are stabilized. In certain embodiments, the curing time can be measured as the time until a size stabilized particle size is reached under a specified test condition. For example, a suitable curing time may be such a time wherein the D50 of the (complexed) drug particles do not change or substantially change after time in consecutive measurements separated by approximately 72 hours, e.g., by more than the accuracy of the measuring instrument (5-10%) in 72 hours after the curing period. Preferred curing times are 1-20 days, 2-15 days or 3-10 days. In other embodiments, the a suitable curing time may be such a time wherein the D50 of the (complexed) drug particles do not change or substantially change after time in consecutive measurements over 1 hour at 37° C. in simulated nasal fluid or pulmonary fluid. The term "complexed" or "complexed nanopartriculate drug" indicates an association of molecules and/or a particle including drug, a complexing agent and other components which results in better particle size stability of drug particles or some other desirable effect. In some cases, complexing agents initially increase particle size (D50) before imparting stability or other beneficial attributes to the formulation. In certain embodiments, complexed drug or complexed nanoparticulate drug made by adding complexing agents requires a curing time.

"Complexing agents" are small molecular weight molecules which after suitable curing time impart additional stability to the drug. Complexing agents include small compounds under MW 550. Complexing agents include but are not limited to the group consisting of phenol, parabens, ascorbic acid, methyl anthranilate, salicylic acid, acetosalicyclic acid, tocopherol, organic acids, carboxylic acids, aromatic acids, aromatic esters, acid salts of amino acids, benzaldehyde, cinnimaldehyde, imidazole, menthol, thiophenol, m-aminobenzoic acid, anthranilic acid, picolinic acids and alkyl esters thereof, toluidides, sodium benzoate, methylparaben, sodium methylparaben, para-aminobenzoic acid and esters, sorbic and benzoic acids, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, esters, isomeric compounds thereof, pharmaceutically acceptable salts thereof, and mixtures of any of the foregoing.

The term "disintegrate" is the dispersion of the dosage form when contacted with physiological fluid present at the site of administration. "Disintegration agents or disintegrants" facilitate the breakup or disintegration of a formulation. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate (Explotab®), bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the nasal cavity into the surrounding tissues.

"Effective particle size" and "particle size" is interchangeably used with "D50". By "D50", it is meant that 50% of the particles are below and 50% of the particles are above a defined measurement. D50 can be used to describe different parameters (volume, length, number, area . . . etc). "Effective particle size" or D50 as used herein indicates the volume-weighted median diameter as measured by a laser/light scattering method or equivalent, wherein 50% of the particles, by volume, have a smaller diameter, while 50% by volume have a larger diameter. The volume weighted D50 also relates to the percentage of weight of the particle under a certain size. For example a D50 of 500 nm means that 50% of the particulate mass is less than 500 nm in diameter and 50% of the particulate mass is greater than 500 nm in diameter. The effective particle size is measured by conventional particle size measuring techniques well known to those skilled in the art. Such techniques include, for example, sedimentation field flow fractionation, photon correlation spectroscopy, light scattering (e.g., with a Microtrac UPA 150), laser diffraction and disc centrifugation. For the purposes of the compositions, formulations and methods described herein, effective particle size is the volume median diameter as determined using laser/light scattering instruments and methods, e.g. a Horiba LA-910. Similarly, "D90" is the volume-weighted diameter, wherein 90% of the particles, by volume, have a smaller diameter, while 10% by volume have a larger diameter and "D10" is the volume-weighted diameter, wherein 10% of the particles, by volume, have a smaller diameter, while 90% by volume have a larger diameter. It is sometimes useful to express the D50 value after sonication for 1 minute or less using about 40 watts of sonicating power at room temperature (25° C.).

The term "grinding media" refers to the material used in milling to physically reduce the particle size of a composition. For milling operations, preferred grinding media are spherical balls of yttrium stabilized zirconium oxide, glass or a plastic resin.

"Simulated Fluid" is simulated fluid at the site of dissolution of the drug of a subject, nasal fluid, pulmonary or the saliva of a subject or the equivalent thereof. An equivalent of nasal fluid is "simulated nasal fluid" is an in vitro fluid having similar content and/or pH as solution in water containing about 7.5 mM monosodium phosphate anhydrous, about 3 mM of disodium phosphate anhydrous, about 150 mM sodium chloride, about 40 mM potassium chloride and about 5 mM calcium chloride at a pH of about 6.4.

"Immediate Release" means a dosage form that releases at least 80% of drug within 2 hours of administration, more specifically, within 1 hour of addition to a commonly accepted simulated fluid.

"Ionic Dispersion Modulator" is defined as a salt (not a sulfonic acid), which when added to a complexed small particle composition will reduce the amount of certain ingredient(s) needed to minimize particle size growth or aggregation of solid dosage forms or blends when dispersed in water or simulated fluids.

"Milling chamber void volume" is the open volume in a milling chamber available to the milling slurry after grinding media has been added. Milling chamber void volume is related to the amount of grinding media (volume %) and the volume of open space when the spherical beads are stacked on one another (grinding media void volume). For 0.2-0.4 mm spherical milling grinding media, a range of approx. 36-42% of the volume occupied by the grinding beads is the grinding media void volume. Milling chamber void volume (mL)=Total milling chamber volume (mL)−volume of grinding media (mL)+grinding media void volume (mL).

"Milling residence time" is the time that a particle is present in the milling chamber over the total time of milling to obtain desired particles. Milling Residence Time (MRT) is defined as: MRT (minutes)=Milling chamber void volume (ml)×total milling time (minutes.)/Milling Slurry Vol. (ml)

The term "milling slurry" refers to a suspension containing the drug for particle size reduction and other ingredients to facilitate the milling process. The composition of the milling slurry is usually not the final formulation composition.

The term "milling media" refers to the components of the milling slurry minus the active pharmaceutical ingredient(s).

The term "milled slurry" refers the milling slurry after it had been reduced to a small particle suspension by milling. The most preferred milling slurries for a liquid dispersion are those that meet particle size and compositions that can be diluted with water and appropriate ingredients to obtain the final formulation. For a solid dosage form, preferred milled slurries are those that can be utilized with minimal manipulation to yield the final solid dosage form.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Preservatives" are compounds which inhibit microbial growth and are typically added to dispersions to prevent microbes from growing.

"Pharmacokinetic parameters" are parameters which describe the in vivo characteristics of the drug over time, including, for example plasma concentration of the drug. Pharmacokinetic parameters include $C_{max}$, $T_{max}$, and $AUC_{0-\tau}$ (each discussed above).

"Solubilizers" include compounds such as triacetin, triethylcitrate, ethyl oleate, ethyl caprylate, sodium lauryl sulfate, sodium docusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200 to 600, glycofurol, transcutol, propylene glycol, and dimethyl isosorbide, miglyol, glycerin, glycerol, and the like.

"Spray Drying" is a process by which a solvent is removed from a composition yielding a dried form of the ingredients in that composition. Drying is effected by spraying the composition through a nozzle into a heated environment containing a vacuum or a flow of air or inert gas. Spray drying can produce amorphous or crystalline powders of drugs or granulations, both which can be converted into a solid dosage form by those skilled in the art.

"Spray Granulation" is a procedure where a solution or suspension containing ingredients are sprayed through a nozzle into a fluidized bed containing excipients(s) which then form granules containing the composition of the solution or suspension with the excipients(s) as the solvent is removed by the flow of a heated gas. Spray Granulation typically involve spraying the solution or suspension onto an excipients (e.g. comprised of a sugar(s) and starch or cellulosics or combinations thereof.

"Size-stabilized" means the D50 does not substantially change (greater than 50%) after an initial time is defined (e.g., after an appropriate curing time) and up to 4 months storage at room temperature (25° C.). For example, the size stabilized drug particles described herein in an aqueous dosage form will not show an increase in effective particle size of greater than 50% over a four month storage period, and preferably no increase in effective particle size of greater than 50% over a two year storage period. Similarly, the size-stabilized drug particles described herein in a liquid or will show an increase in effective particle size of about 0% to about 100% upon dispersion in simulated nasal fluid as compared to the initial D50 value. In solid forms the size-stabilized drug particles described herein in a liquid or will show an increase in effective particle size of about 0% to about 100% upon dispersion in simulated nasal fluid as compared to the D50 when dispersed in water (deionized or distilled). In some embodiments, the formulations described herein does not produce any significant amount of unidentified drug degradation impurities up to 4 months storage at room temperature (25° C.) at individual levels of about greater than 0.1% by weight as compared to the impurity levels at the initial time designation.

"Surface Stabilizers" are non-crosslinked excipients associated with the surface of the small particle to stabilize the composition from significant particle size growth and/or agglomeration. Generally, surface stabilizers fall into two categories: non-ionic (also called stearic stabilizers or modifiers) and ionic stabilizers. The most common non-ionic stabilizers are excipients which are contained in classes known as binders, fillers, surfactants and wetting agents. Limited examples of non-ionic surface stabilizers are hydroxypropylmethyl cellulose, polyvinylpyrrolidone, Plasdone, polyvinyl alcohol, Pluronics, Tweens and Polyethyleneglycols (PEGs) s. A subset of surface stabilizers commonly used is ionic in nature. These ionic surface stabilizers tend to fall into the class of excipients which are typically used as surfactants and wetting agents. Ionic stabilizers used in the prior art are typically organic molecules bearing an ionic bond such that the molecule is essentially fully charged in the formulation. The two most described ionic surface stabilizers are the long chain sulfonic acid salts sodium lauryl sulfate and dioctyl sodium sulfosuccinate (DOSS). Surface stabilizers are further defined in certain embodiments as encompassing the definitions and materials described in PCT/US2006/046035 filed Dec. 4, 2006 claiming priority from U.S. Provisional Application No. 60/741,452, both of which are hereby incorporated by reference.

"Subject" as used herein is any mammal. Subjects include individuals in need of drug treatment (patients) and individuals not in need of drug treatment (e.g. normal healthy volunteers. Humans are preferred subjects and patients.

A "therapeutically effective amount" or "effective amount" is that amount of a pharmaceutical agent to achieve a pharmacological effect. The term "therapeutically effective amount" includes, for example, a prophylactically effective amount. An "effective amount" of drug is an amount needed to achieve a desired pharmacologic effect or therapeutic improvement without undue adverse side effects. The effective amount of a drug will be selected by those skilled in the art depending on the particular patient and the disease. It is understood that "an effect amount" or "a therapeutically effective amount" can vary from subject to subject, due to variation in metabolism of drug, age, weight, general condition of the subject, the condition being treated, the severity of the condition being treated, and the judgment of the prescribing physician.

"Treat" or "treatment" refers to any treatment of a disorder or disease, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or reducing the symptoms of the disease or disorder.

"Wetting agents" include surfactants and are used to enhance the dispersion of a drug in a composition or after administration of the composition to a subject. Wetting agents can also act as stabilizers. Examples of wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

BRIEF DESCRIPTION OF THE DRAWINGS

FIG. 1 is a graph of the particle size distribution of mometasone furoate anhydrous nanosuspension formulations of Examples 2 and 1, respectively (complexed and uncomplexed) after incubation in simulated nasal fluid at 37° C. for 15 minutes.

FIG. 2 is a graph of the particle size distribution of mometasone furoate anhydrous nanosuspension formulations of Examples 2 and 1, respectively (complexed and uncomplexed)after incubation in simulated nasal fluid at 37° C. for 30 minutes.

FIG. 3 is a graph of the DSC value for traces of mometasone furoate anhydrous (A) and mometasone furoate monohydrate (B) heated at 10° C./min.

FIG. 4 is a graph of the x-ray powder diffraction patterns of mometasone furoate anhydrous (A) and mometasone furoate monohydrate (B).

FIG. 5 is a graph of the particle size distribution of mometasone furoate monohydrate nanosuspension formulations of Example 6 (complexed and uncomplexed) after incubation in simulated nasal fluid at 37° C. for 15 minutes.

FIG. 6 is a graph of the particle size distribution of mometasone furoate monohydrate nanosuspension formulations of Example 6 (complexed and uncomplexed) after incubation in simulated nasal fluid at 37° C. for 30 minutes.

Figure 7:
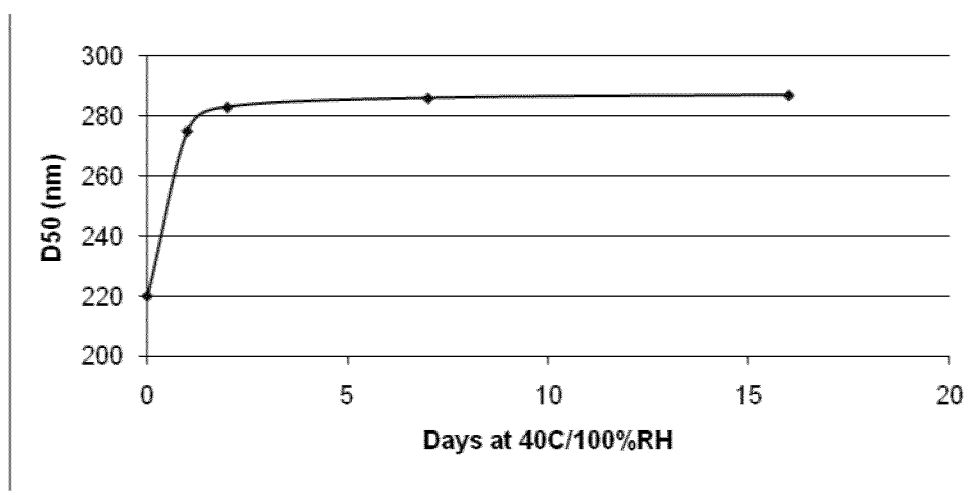

FIG. 7 is a graph of the D50 values (nm) of a complexed mometasone furoate monohydrate nanosuspension of Example 7 in deionized water under accelerated storage conditions (40° C./100% RH)

DETAILED DESCRIPTION

Enhancing stability has been the focus of much research. Stability is a broad reference and in the pharmaceutical industry is generally recognized as testing needed to determine storage stability (the stability of the formulation under storage over time), purity stability (the purity profile of the formulation over storage conditions), release or dispersion stability (the stability of release or disintegration characteristics for the formulation in water and physiological media). The physiological media for dispersion stability is dependent on the route of administration (simulated gastric and/or intestinal fluid for oral products, saliva for buccal and sub-lingual products, nasal fluid for intranasal products . . . etc). In general any parameter important to the performance or tolerability of a formulation must be monitored for stability. The potential advantages of nanoparticulate corticosteroid compositions are possible if the drug particles do not aggregate substantially in the physiological media to which the product is exposed.

In Applicants' U.S. patent application Ser. No. 11/998,362, entitled "Nanoparticulate formulations and methods for the making and use thereof", filed Nov. 28, 2007; U.S. patent application Ser. No. 11/606,222, entitled "Solid ganaxolone formulation and methods for the making and use thereof", filed Nov. 28, 2006; and U.S. patent application Ser. No. 11/605,700, "Liquid ganaxolone formulation and methods for the making and use thereof", filed Nov. 28, 2006, the disclosures of which are hereby incorporated by reference in their entirety, Applicants disclosed that certain insoluble and lipophilic drugs when formulated with conventional methodology (non-ionic or ionic surface stabilizers) in a nanoparticulate composition could demonstrate reasonable storage stability and show substantial aggregation in physiological media. To solve this issue a new form of agent (Complexing agent) was discovered which imparted substantially better stability in physiological media or under heat or cold stressing by initially involving a curing process where the particle size increases during the curing process and then becomes size stabilized where it is much less prone to agglomeration than the non-complexed particles.

In certain embodiments, the present invention is directed to complexed corticosteroid particles having a volume weighted median diameter (D50) from about 50 nm to about 500 nm, each of the particles comprising in association (i) a nonionic surface stabilizer and (ii) an ionic surface stabilizer and (iii) a complexing agent where the particles are cured for at least about 3 days.

Corticosteroid suitable for use in the present invention may include, but are not limited to, budesonide, triamcinolone acetonide, triamcinolone, mometasone, mometasone furoate, flunisolide, fluticasone propionate, fluticasone, beclomethasone dipropionate, dexamethasone, triamincinolone, beclomethasone, fluocinolone, fluocinonide, flunisolide hemihydrate, mometasone furoate monohydrate, clobetasol, and any pharmaceutically acceptable salts, hydrates, polymorphs and combinations thereof.

Suitable complexing agents for use in the present invention, include but are not limited to, parabens, organic acids, carboxylic acids, aromatic acids, aromatic esters, acid salts of amino acids, methyl anthranilate, anthranilic acid sodium metabisulphite, ascorbic acid and its derivatives, malic acid, isoascorbic acid, citric acid, tartaric acid, sodium sulphite, sodium bisulphate, tocopherol, water- and fat-soluble derivatives of tocopherol, sulphites, bisulphites and hydrogen sulphites, para-aminobenzoic acid and esters, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, propyl/gallate, nordihydroguaiaretic acid, phosphoric acids, sorbic and benzoic acids, esters, ascorbyl palmitate, derivatives and isomeric compounds thereof, pharmaceutically acceptable salts thereof, and mixtures thereof. The complexing agent may be included in an amount effective to cause an initial increase in the size of the particles, wherein the volume weighted median diameter (D50) of the particles before the initial growth is from about 50 to about 250 nm and the D50 at the end of the curing time is 15% to 100% larger than the D50 measured before the curing period. For example, in certain embodiments, the complexing agent is included in an amount from about 0.1% to about 25% w/w of the size-stabilized drug particles. The complexing agent may be included in an amount form about 0.1% to 8% w/w of the size-stabilized drug particles.

In certain embodiments, the volume weighted diameter (D50) of the complexed particles does not change by more than 10% after a time in consecutive measurements separated by about 72 hours.

In certain embodiments, the complexed particles increase in effective particle size from about 0% to about 100% upon dispersion in simulated nasal or pulmonary fluid as compared to initial values (suspension) or a dispersion in water under the same conditions (for dry complexed particle compositions).

In the prior art, large ranges of surface stabilizers are claimed as well wide concentration ranges for aqueous suspensions. As the doses of corticosteroids are quite small (50-250 microgram/dose), the prior art does not teach about amounts of stabilizers necessary to stabilize a nanoparticulate suspension when the concentration of active ingredient(s) are low. To assess the feasibility of maintaining a nanoparticulate dispersion for commercial use, one must examine the storage and dispersion stability at the physiological concentrations required. Additionally, it is desirable to apply intranasal corticosteroids in an isotonic suspension to soothe the nose and also minimize aggregation when the suspension is subjected to abrupt changes in isotonicity. Addition of sodium chloride to nanoparticulate suspensions at appropriate concentrations results in increased aggregation as the sodium chloride functions to salt out or lower the cloud point of certain stabilizers making the composition less stable. As the allowed quantity and types of agents that can be used in intranasal and inhaled applications are limited, this makes creation of a non-aggregating commercially viable corticosteroid composition at pharmacological doses difficult to exemplify.

In certain preferred embodiments, the drug particles are prepared with the use of one or more materials known in the art as surface stabilizers or modulators (previously or alternatively referred to herein or in the art as wetting and/or dispersing agents) which are, e.g., adsorbed on the surface of the drug compound. The surface stabilizer(s) can be contacted with the drug compound either before, during or after size reduction of the compound. Generally, surface stabilizers fall into two categories: non-ionic (also called steric stabilizers or modifiers) and ionic stabilizers. The most common non-ionic stabilizers are excipients which are contained in classes known as binders, fillers, surfactants and wetting agents. Limited examples of non-ionic surface stabilizers are hydroxypropylmethylcellulose, polyvinylpyrrolidone, Plasdone, polyvinyl alcohol, Pluronics, Tweens and polyethylene glycols (PEGs). A subset of surface stabilizers commonly used is ionic in nature. These ionic surface stabilizers tend to fall into the class of excipients which are typically used as surfactants and wetting agents. Ionic stabilizers used in the prior art are typically organic molecules bearing an ionic bond such that the molecule is charged in the formulation. The two most described ionic surface stabilizers are the long chain sulfonic acid salts sodium lauryl sulfate and dioctyl sodium sulfosuccinate (DOSS). Broad ranges for all surface stabilizers have been claimed in U.S. Pat. No. 5,145,684 (the '684 patent) ranging from 0.1% to 90% by weight of the composition. Typically, one adds 20%-150% (wt % of drug) of a nonionic surface stabilizer and 0.2%-5% of an ionic surface stabilizer (wt % of drug) to achieve maximal particle size stabilization from these surface stabilizers.

Alternatively, the surface stabilizers used in the present invention are defined as comprising one or more hydrophilic polymers and/or one or more wetting agents.

In certain embodiments, the hydrophilic polymer can be selected from the group consisting of a cellulosic polymer, a vinyl polymer and mixtures thereof. Particular hydrophilic polymers include cellulosic polymer such as cellulose ethers (e.g., hydroxypropylmethylcellulose.) or a vinyl polymer such as polyvinyl alcohol.

In certain embodiments, the wetting agent can be selected from the group consisting of sodium lauryl sulfate, a pharmaceutically acceptable salt of docusate, and mixtures thereof.

Formulations

The corticosteroid complexed particles of the present invention may be incorporated into various pharmaceutical formulations.

In certain embodiments, the present invention provides for a pharmaceutical composition comprising the corticosteroid complexed particles described above together with at least one pharmaceutically acceptable excipient. In certain embodiments, the pharmaceutical composition may be in the form of a solid dosage form. In other embodiments, the pharmaceutical composition may be in the form of a liquid dosage form, e.g., suspension.

Intranasal and Inhalation Formulations

In other preferred embodiments the corticosteroid complexed particles may be incorporated into an intranasal or inhalation dosage form and administered, for example, by oral inhalation or intranasally to treat disease of the lower and/or upper airway passages and/or lungs. These intranasal and inhalation dosage forms (or delivery devices) may further include pharmaceutically acceptable excipients suitable for use for intranasal and inhalation delivery of the corticosteroid complexed particles to a patient in need thereof.

The delivery devices found useful for providing measured substantially non-systematically bioavailable amounts of aerosolized corticosteriods or aerosolized pharmaceutical compositions thereof for delivery to the oral airway passages and lungs by oral inhalation or intranasally by inhalation include, for example, pressurized metered-dose inhalers ("MDI") which deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents; dry-powder inhalers either breath activated or delivered by air or gas pressure such as the dry-powder inhaler disclosed in the Schering Corporation International Patent Application No. PCT/US92/05225, published 7 Jan. 1993 as well as the TURBUHALER™ (available from Astra Pharmaceutical Products, Inc.) or the ROTAHALER™ (available from Allen & Hanburys) which may be used to deliver the aerosolized mometasone furoate as a finely milled powder in large aggregates either alone or in combination with some pharmaceutically acceptable carrier e.g. lactose; and nebulizers.

The inhalation of aerosolized drugs by use of nebulizers and metered-dose inhalers such as used to deliver VANCENASE® (brand of beclomethasone dipropionate) inhalation aerosol (available from Schering Corporation, Kenilworth, N.J.) is disclosed in Remington's Pharmaceutical Sciences, Mack Publishing Co. Easton Pa., 15th Ed. Chapter 99, pages 1910-1912.

The corticosteroids utilized in the present invention, e.g., mometasone furoate, may be also administered in specific, measured amounts in the form of an aqueous suspension by use of a pump spray bottle such as the bottles used to deliver VANCENASE AQ® Nasal Spray as well as the spray bottle disclosed in the Schering Corporation Industrial Design Deposit DM/026304, registered by the Hague Union on Jun. 1, 1993 (each are available from Schering Corporation). The aqueous suspension compositions of the present invention may be prepared by admixing the corticosteroid, e.g., mometasone furoate or mometasone furoate monohydrate (preferably mometasone furoate monohydrate) with water and other pharmaceutically acceptable excipients as disclosed in International Application No. PCT/US91/06249, the disclosure of which is hereby incorporated by reference, for preparation of mometasone furoate monohydrate and aqueous suspensions containing same.

When incorporated into a pharmaceutical composition comprising pharmaceutically acceptable excipients, the amount of drug complexed particles may range from about 0.005% to about 80%, based on the weight of the entire composition and the amount of each pharmaceutically acceptable excipient may range from about 0.01% to about 80% based on the weight of the total composition.

One skilled in the art would recognize the dose of corticosteroid required per gram of suspension in the aqueous suspensions of the present invention. For example, when mometasone is utilized in an aqueous suspension, the aqueous suspension may contain from about 0.01 to 10.0 mg, preferably 0.1 to 10.0 mg of mometasone furoate monohydrate per gram of suspension.

The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phospate as well as mixtures of citrate and phosphate buffers; surfactants, e.g. Polysorbate 80; and antimicrobial preservatives, e.g., benzalkonium chloride, phenylethyl alcohol and potassium sorbate.

Other suitable vehicles for the formulations according to the invention include aqueous solutions containing an appropriate isotoning agent selected among those commonly used in pharmaceutics. Substances used for this purpose are, for instance, sodium chloride and glucose. The quantity of isotoning agent should impart to the vehicle (taking into account the osmotic effect of the active ingredient), an osmotic pressure similar to that of biological fluids, i.e. generally from about 150 to about 850 milliOsmoles (mOsm) preferably from about 270 to about 330 mOsm.

However, it is known that nasal mucous membranes are also capable of tolerating slightly hypertonic solutions.

Should a suspension or gel be desired instead of a solution, appropriate oily or gel vehicles may be used or one or more polymeric materials may be included, which desirably should be capable of conferring bioadhesive characteristics to the vehicle.

Several polymers are used in pharmaceutics for the preparation of a gel; the following can be mentioned as nonlimiting examples: hydroxypropyl cellulose (KLUCEL®), hydroxypropyl methyl cellulose (METHOCEL®), hydroxyethyl cellulose (NATROSOL®), sodium carboxymethyl cellulose (BLANOSE®), acrylic polymers (CARBOPOL®, POLYCARBOPHIL®), gum xanthan, gum tragacanth, alginates and agar-agar.

Some of them, such as sodium carboxymethyl cellulose and acrylic polymers, have marked bioadhesive properties and are preferred if bioadhesiveness is desired.

Other formulations suitable for intranasal administration of the corticosteroid complexed particles can be obtained by adding to the aqueous vehicle polymers capable of changing the rheologic behavior of the composition in relation to the temperature. These polymers make it possible to obtain low viscosity solutions at room temperature, which can be applied for instance by nasal spray and which increase in viscosity at body temperature, yielding a viscous fluid which ensures a better and longer contact with the nasal mucous membrane. Polymers of this class include without limitation polyoxyethylene-polyoxypropylene block copolymers (POLOXAMER®).

In addition to aqueous, oil or gel vehicles, other vehicles which may be used in the compositions according to the invention comprise solvent systems containing ethyl alcohol, isopropyl alcohol, propylene glycol, polyethylene glycol, mixtures thereof or mixtures of one or more of the foregoing with water.

In any case, a pharmaceutically acceptable buffer should be present in order to create optimum pH conditions for both product stability and tolerance (pH range about 4 to about 8; preferably about 5.5 to 7.5). Suitable buffers include without limitation tris (tromethamine) buffer, phosphate buffer, etc.

Other excipients include chemical enhancers such as absorption promoters. These include chelating agents, fatty acids, bile acid salts and other surfactants, fusidic acid, lysophosphatides, cyclic peptide antibiotics, preservatives, carboxylic acids (ascorbic acid, amino acids), glycyrrhetinic acid, o-acylcarnitine. Preferred promoters are diisopropyladipate, POE(9) lauryl alcohol, Tween 80, EDTA, sodium glycocholate and lysophosphatidyl-choline which proved to be particularly active. Finally, the new compositions according to the invention preferably contain preservatives which ensure the microbiological stability of the active ingredient. Suitable preservatives include without limitation, methyl paraben, propyl paraben, sodium benzoate, benzyl alcohol, benzalkonium chloride and chlorobutanol.

The liquid corticosteroid complexed particle formulations, preferably in the form of solutions, may be administered in the form of drops or spray, using atomizers equipped with a mechanical valve and possibly including a propellant of a type commercially available, such as butane, N.sub.2, Ar, CO.sub.2, nitrous oxide, propane, dimethyl ether, chlorofluorocarbons (e.g. FREON) etc. Vehicles suitable for spray administration are water, alcohol, glycol and propylene glycol, used alone or in a mixture of two or more.

One advantage of using the corticosteroid complexed particles of the present invention is that their use in the various formulations (e.g., intranasal or inhalation devices) provides a faster onset of action, e.g., within 5 hours, as compared to other marketed corticosteroid products.

Use of the corticosteroid complexed particles also makes it possible to administer ⅓ to ½ the dose needed to achieve the same efficacy as compared to other marketed corticosteroids.

Methods of Treatment

The present invention is also directed to the use of the corticosteroid complexed particles for the treatment of various disease states and/or conditions. For example, the corticosteroid complexed particles may be utilized to treat asthma, chronic obstructive pulmonary disease, granulomatous diseases, idiopathic pulmonary fibrosis, hypersensitivity pneumonitis, bronchopulmonary dysplasia, and any other disease or condition affecting the respiratory pathway and requiring the treatment with corticosteriods.

In certain preferred embodiments, the corticosteroid complexed particles utilized for treating the above-mentioned disease states and/or conditions may contain mometasone, mometasone furoate anhydrous, mometasone furoate monohydrate, and pharmaceutically acceptable salts, hydrates, polymorphs and combinations thereof. The use of mometasone for the treatment of these various diseases states an/or conditions is described in U.S. Pat. No. 6,949,532 (to Schering Corporation), entitled "Use of mometasone furoate for treating airway passage and lung diseases", filed Jan. 22, 2004, the disclosure of which is hereby incorporated by reference.

Based on the judgment of the attending clinician, the amount of mometasone furoate administered and the treatment regimen used will, of course, be dependent on the age, sex and medical history of the patient being treated, the severity of the specific asthmatic or non-malignant pulmonary disease condition and the tolerance of patient to the treatment regimen as evidenced by local toxicity (e.g., nasal irritation and/or bleeding) and by systemic side-effects (e.g. cortisol level). Cortisol (also referred to as hydrocortisone) is the major natural glucocorticosteroid elaborated by the adrenal cortex.

Typically, for the treatment of allergic, non-allergic rhinitis and/or inflammatory diseases of the upper or lower airway passages to treat for example asthma or allergic or non-allergic rhinitis, the substantially non-systematically bioavailable amount of mometasone furoate which may be administered as an aqueous suspension or dry powder is in the range of about 10 to 5000 micrograms ("mcg")/day, 10 to 4000 mcg/day, 10 to 2000 mcg/day, 25-1000 mcg/day, 25 to 400 mcg/day, 25-200 mcg/day, 25-100 mcg/day or 25-50 mcg/day in single or divided doses. However, with the mometasone complexed particles of the present invention, the above-mentioned dosages may be reduced by ⅓ to ½.

In treating allergic and non-allergic rhinitis, the aqueous suspension of mometasone furoate may be administered intranasally by inserting an appropriate device (such as the pump spray bottle used to deliver Vancenase AQ®. Nasal Spray as well as the spray bottle disclosed in the Schering Corporation Industrial Design Deposit DM/026304 registered Jun. 1, 1993) into each nostril. Active drug is then expelled (nasal spray device) or could be nasally inhaled (sniffed) as a powder. Efficacy is generally assessed in a double blind fashion by a reduction in nasal symptoms (e.g., sneezing, itching, congestion, and discharge). Other objective measurements (e.g., nasal peak flow and resistance) can be used as supportive indices of efficacy.

Typically, for treatment of allergic and/or inflammatory diseases of the lower airways and lung parenchyma especially diseases such as asthma, chronic obstructive pulmonary disease ("COPD"), granulomatus diseases of the lungs and lower airway passage, non-malignant proliferative disease of the lungs e.g., idiopathic pulmonary fibrosis, hypersensitivity pneumonitis and bronchopulmonary dysplasia the following dosage ranges of mometasone furoate may be used: (1) for metered dose inhalers with standard CFC or alternate propellant about 10 to 5000 mcg/day or 10 to 4000 mcg/day or 10 to 2000 mcg/day, or 50 to 1000 mcg/day or 25 to 100 mcg/day, or 25 to 400 mcg/day, or 25 to 200 mcg/day, or 25-50 mcg/day; the preferred dosage range is 50 to 1000 micrograms a day and the preferred dosages are 25, 100, 200 and 250 mcg, administered in one to four puffs; preferably one to three puffs, once-a-day; (2) for the dry powder inhaler--about 10 to 5000 mcg/day or 10-4000 mcg/day or 10-2000 mcg/day or 25-1000 mcg/day or 25-400 mcg/day or 25-200 mcg/day or 50-200 mcg/day or 25-50 mcg/day of anhydrous mometasone furoate; the preferred dosage range of anhydrous mometasone furoate in the dry powder inhaler is 50 to 600 micrograms a day more preferably 100 to 600 mcg a day and the preferred dosages are 50, 100, 200 and 250 mcg, administered in one to three puffs, once-a-day; typically the metered dose inhaler unit will contain 120 doses; (3) for aqueous suspension for inhalation, the preferred dosage range is from 25 to 800 mcg/100 μl and the dosages are 25, 50, 100, 125, 150, 175, 200, 225, 250, 300, 400, 500 and 800 mcg/100 μL of mometasone furoate in single or divided doses. The aqueous suspension of mometasone furoate has been found to be safe and effective in treating allergic rhinitis e.g. seasonal allergic rhinitis from 25 micrograms up to 1600 micrograms administered once-a-day; the preferred dosage range is 25-800 micrograms a day, although no improvement in treatment is typically found above 400 micrograms a day. The most preferred dosages are 25, 50 and 100 micrograms administered twice to each nostril, once-a-day for a total once-a-day dose of 100, 200 and 400 mcg. Typically 2-4 mL of the aqueous suspension of mometasone furoate monohydrate may be placed in a plastic nebulizer container and the patient would inhale for 2-10 minutes. The total dosage placed in such a container would be in the range of 300-3000 mcg. However, with the mometasone complexed particles of the present invention, the above-mentioned dosages may be reduced by ⅓ to ½.

In another aspect of this invention, the anhydrous mometasone furoate may be admixed with a dry excipient, for example dry lactose for use in the dry powder inhaler. The mometasone furoate: dry lactose ratio varies broadly from 1:19 to 1:0, and preferably it is 1:19 to 1:4. Typically, the suitable anhydrous mometasone furoate dosage range is 25 to 600 micrograms administered once-a-day. The preferred mometasone furoate dosages for admixture with dry lactose are 25, 100, 200 and 250 micrograms which are administered in one to three puffs a day. The preferred combined mometasone furoate: lactose dose is 500 micrograms for each dose. For example, for the preferred 1:19 ratio, 25 micrograms of anhydrous mometasone furoate are admixed with 475 micrograms of anhydrous lactose and for the preferred 1:4 ratio, 100 micrograms of anhydrous mometasone furoate are admixed with 400 micrograms of anhydrous lactose, to produce the 500 microgram dose of the mometasone furoate: lactose admixture.

The dosing regimen for lower airway diseases such as asthma will vary from four times a day to twice a day to once-a-day. Once-a-day (such as at 8 a.m.) maintenance therapy should be adequate, once control of asthma is achieved. It is anticipated, however, that the superior therapeutic index of mometasone furoate will result in effective treatment of patients by once-a-day dosing even at the initiation of the methods of this invention.

For other diseases of the lower airway passages and/or lungs, dosing is likely to be two to four times daily, preferably two to three times and most preferably once daily, when adequate control of the disease is achieved.

For any route of administration, divided or single doses may be used. For example, when a metered dose inhaler is used to deliver, for example, 500 mcg of aerosolized mometasone furoate, once-a-day, two puffs of 250 mcg would normally be used to deliver the aerosolized drug. When a plastic nebulizer container is used to deliver for example 200 micrograms a day of an aqueous suspension of mometasone furoate, two squeezes of 50 micrograms into each nostril would normally be used to deliver the drug. When the metered dose inhaler is used to deliver for example 200 mcg of anhydrous mometasone furoate, two puffs of 500 micrograms of an admixture of 100 mcg of mometasone furoate and 400 mcg of lactose once-a-day would normally be used to deliver the aerosolized drug. In addition to the faster onset, the corticosteroid complexed particle formulations of the present invention may be more effective in relieving nasal congestion as well as symptoms of the eye from allergic rhinitis.

DETAILED DESCRIPTION OF THE PREFERRED EMBODIMENTS

The invention will be further appreciated with respect to the following non-limiting examples. Other variations or embodiments of the invention will also be apparent to one of ordinary skill in the art from the above descriptions and examples. Thus the foregoing embodiments are not meant to be construed as limiting the scope of the invention.

Experimental Section:

Preparation of Simulated Nasal Fluid (SNF)

In a 500 mL volumetric flask were placed monosodium phosphate anhydrous (447 mg), disodium phosphate anhydrous (210 mg), sodium chloride (4.4 g), potassium chloride (1.5 g) and calcium chloride (dihydrate, 368 mg). Deionized water was added to dissolve the solids and to establish the final volume. The pH of the solution was approximately 6.4.

Particle Size Measurement Method

The following methods and settings for particle size measurement were used.

Particle Size Method using Horiba Laser Scattering Particle Size Distribution Analyzer LA-910

Particle size measurement using Horiba laser scattering particle size distribution analyzer is generally well known for those skilled in the art. It is important that the parameters be kept constant when measuring different samples if they are used for comparison purposes. For corticosteroid nanoparticulate compositions, instrument settings and sample preparation method are described below:

Instrument Settings and Parameters:

Measure Conditions: Circulation=4; ultrasonic time=1; agitation=1; sampling times: red laser=10, blue lamp=2; preferred % transmittance: blue lamp=75-80%; blank: red laser=10, blue lamp=2. For D50 values after sonication, the sonication power is set to low and the sonication time is 1 minute.

Display Settings:

Form of distribution: standard (Gaussian)=10 iterations; RR Index=1.15-010; distribution base: volume; size class=passing (underclass).

Sample Preparation and Particle Size (D50) Determination

For concentrated nanoparticle drug suspensions, dilute the nanoparticulate composition with deionized water to approximately 5 mg/mL API concentration. Shake well for 15-30 seconds. Add 120 mL of deionized water to the chamber, turn agitation and recirculation settings on. Transfer the nanoparticulate suspension via a pipette to the sample chamber in sufficient quantity to reach the transmittance range of 75-80% blue lamp. If a suspension or stability indicating dispersion is at a concentration of approximately 0.5 mg/ml or lower do not further dilute if not necessary and use directly for particle size measurement. Transfer the sample to be measured via a pipette to up to the desired transmittance range (75-80% blue lamp). Take a measurement and collect the D50 value. This will be the unsonicated particles size. Sonicate for 1 min and take a measurement again to collect D50 value. This will be the particle size after 1 minute sonication. One can also use this procedure obtain other particle size parameters such as D10 or D90 values. If the concentration of corticosteroid to be tested is lower than 1 mg/ml then no dilution is needed and the suspension can be tested directly in the chamber with little or no water to achieve the desired transmittance range.

Example 1

Preparation of Uncomplexed Nanoparticulate Mometasone Furoate Anhydrous

Mometasone furoate (1.92 g, APAC Pharmaceutical, LLC) was slurried in a milling medium (36.1 g) containing 5% HPMC, 0.1% SLS and ca 30 ppm of simethicone for ca 1 h. The fully dispersed slurry was slowly poured into a grinding bottle containing 75.6 mL of polystyrene PB-4 beads (0.15-0.25 mm, GlenMills). The content in the bottle was agitated by hand-turning the stir shaft to ensure complete wetting of the beads and removal of air trapped in the beads. The grinding bottle was then tightly closed and fitted into a larger plastic bottle (cooling bottle) filled with ice-water. The cooling bottle was then mounted onto a blender (Hamilton Beach Commercial) for grinding. The blender was operated at low power setting in an on-off fashion (on for 1 min and off for 2 min) to avoid overheating. The grinding process was monitored by particle size measurement using a Horiba LA-910 particle size analyzer (Irvine, Calif.). The data are presented in Table 1. The milled mometasone furoate slurry was recovered by filtering off the polystyrene beads through a 2.7 µm glass microfiber filter (Whatman GF/D Circles, 47 mm, Cat. #1823047) under vacuum. A white suspension (23.1 g) with a D50 of 110 nm was obtained. The mometasone furoate concentration was approximately 5% w/w.

TABLE 1

Table 1: D50 value change with grinding time

| Total grinding Time (min) | D50 (nm) with no sonication | D50 (nm) after 1 min sonication |
|---|---|---|
| 8 | 214 | ND |
| 12 | 154 | 151 |
| 16 | 122 | 121 |
| 20 | 117 | 117 |

ND: Not Determined

Example 2

Preparation of a Complexed Mometasone Furoate Anhydrous Nanoparticulate Suspension The mometasone furoate nanoparticulate suspension of Example 1 (1g) was diluted with deionized water (9 g) followed addition of methylparaben sodium (11.5 mg). The resultant suspension was shaken to mix well. Citric acid anhydrous (12.7 mg) was then added to achieve 0.1% methylparaben (w/w) and pH4. The mometasone furoate concentration was approximately 0.5% w/w. The suspension was kept at ambient for particle size to stabilize (Table 2).

TABLE 2

Table 2: D50 values of Mometasone furoate nanosuspension in the presence of methylparaben sodium and citric acid

| | D50 (µm) | |
|---|---|---|
| Days at ambient | No sonication | 1 min sonication |
| 0 | 0.11 | 0.11 |
| 4 | 0.136 | 0.137 |
| 5 | 0.138 | 0.138 |
| 7 | 0.135 | 0.135 |
| 11 | 0.162 | 0.154 |
| 63 | 0.148 | 0.148 |

Example 3

Stability of Complexed Mometasone Furoate Nanoparticulate Suspension Versus the Uncomplexed Suspension when Dispersed in Simulated Nasal Fluid (SNF) at 37° C.

Figure 2:
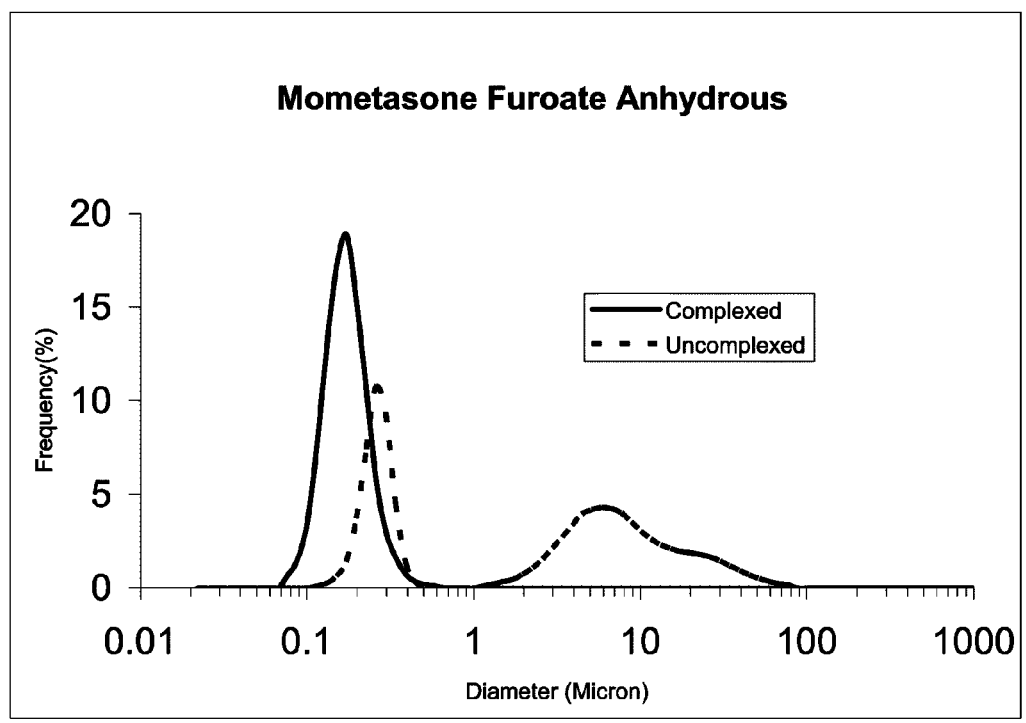

The uncomplexed mometasone suspension of Example 1 was diluted 10-fold with deionized water and 1 gm of the resulting suspension was diluted another 10-fold (addition of 9 gm deioinzed water). The complexed mometasone nanaoparticulate suspension of Example 2 (1g) and deioinzed water (9 g each) were mixed to obtain mometasone furoate nanosuspensions at pharmacologically relevant concentrations (approximately 0.05% w/w mometasone furoate). The two suspensions were incubated side by side in SNF at a concentration of ca 0.25 mg/mL at 37° C. The particle size distribution curves of the complexed and uncomplexed mometasone furoate nanosuspensions after 15 and 30 min incubation in simulated nasal fluid are shown in FIG. 1 and FIG. 2, respectively. D50 values before and after incubation are shown in Table 3. As demonstrated by the data, the particle size of the complexed mometasone furoate nanoparticles remained unchanged after incubation in SNF at 37° C. The uncomplexed version flocculated under the same conditions.

TABLE 3

Table 3: D50 (D90) values (µm) of complexed and uncomplexed mometasone furoate nanosuspensions before and after incubation in SNF at 37° C.

| | Initial* | After 15 min incubation in SNF | After 30 min incubation in SNF |
|---|---|---|---|
| Complexed mometasone furoate suspension | 0.162 (0.252) | 0.154 (0.224) | 0.158 (0.236) |
| Uncomplexed mometasone furoate suspension | 0.118 (0.188) | 4.027 (33.064) | 3.486 (18.584) |

*D50 (D90) values are for the concentrated stork suspensions

Example 4

Preparation of Mometasone Furoate Monohydrate and Preparation of a Nanoparticulate Suspension Step 1: Conversion of Mometasone Furoate Anhydrous to Mometasone Furoate Monohydrate Mometasone furoate (3.4 g, APAC Pharmaceutical, LLC) was dissolved in 2-propanol (243 mL) at reflux. Deionized water (19.5 mL) was added dropwise through the condenser. The solution was kept at reflux during the water addition. After addition of water, heating was removed and the hot solution was stirred for 1 h and left at ambient overnight unstirred. The next morning, more deionized water (240 mL) was added with stirring. The solution became cloudy and white precipitate began to form. The white suspension was stirred for 1 h after water addition and filtered under vacuum. The white solid was washed with water (20 mL) and dried in a fume hood to a constant weight (3.0 g, 88% yield).

The above mixture (2 g) was slurried in absolute ethanol (350 mL) at 40° C. overnight. The mixture was cooled to room temperature and filtered under vacuum. The white cake was washed with water (20 mL) and dried in air in a fume hood to a constant weight (1.8 g)

Figure 3:
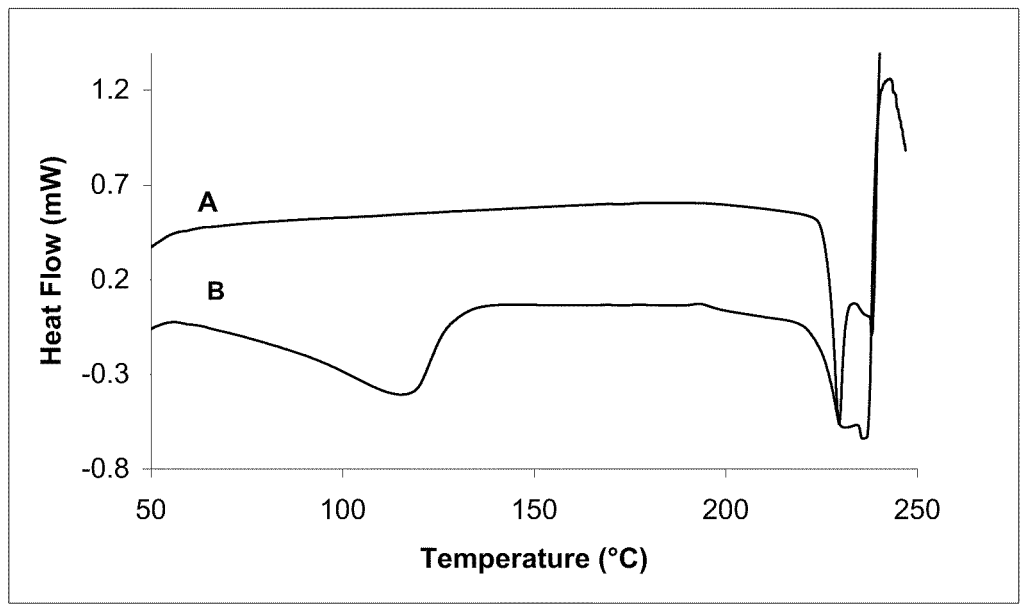
Figure 4:
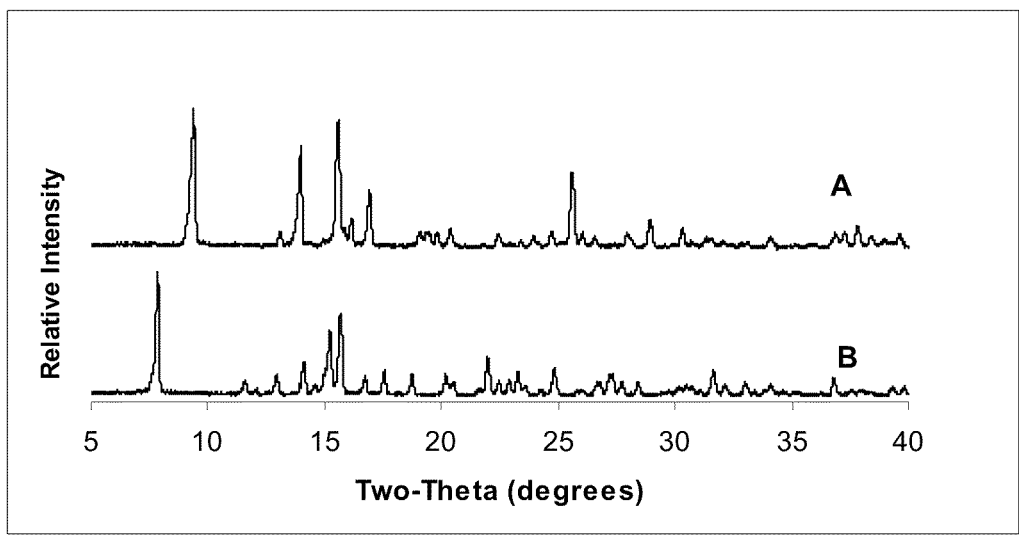

The 1.8 gm was shown to be pure Mometasone Furoate Monohydrate form by DSC and XRPD (FIGS. 3 and 4).

Step 2. Grinding Mometasone Furoate Monohydrate to Obtain Nanoparticulate Suspension Mometasone furoate monohydrate (1.8 g) dispersed in a milling medium (36.1 g) containing 5% HPMC, 0.1% SLS and approximately 30 ppm of simethicone was milled in the same fashion as described in Example 1. After 22 minutes of milling time, the milling mixture was ca 10-fold diluted with deionized water and filtered to obtain a white suspension (325 g) having a D50 value of 192 nm before sonication and 195 nm after 1 minute sonication. The mometasone furoate concentration was determined by HPLC to be 0.41% (w/w) on anhydrous basis.

Example 5

Preparation of Complexed and Non-Complexed Nanoparticulate Suspensions of Mometasone Furoate Monohydrate A sample of the milled mometasone furoate monohydrate suspension from Example 4, Step 2 (100 g) was added methylparaben sodium (113 mg). After thoroughly mixed, citric acid anhydrous (127 mg) was added to achieve 0.1% methylparaben concentration based on the total weight of the suspension. The pH of the suspension was approximately 4.

Half (50 g) of the methylparaben containing mometasone furoate suspension was further added potassium sorbate (50 mg) as a preservative. The two suspensions were kept at ambient for particle size to stabilize (Table 4).

TABLE 4

Table 4: D50 values of mometasone furoate monohydrate nanosuspensions at ambient temperature in the presence of 0.1% (w/w) methylparaben with or without 0.1% (w/w) potassium sorbate.

| | D50 (µm) | | | |
|---|---|---|---|---|
| | No potassium sorbate | | 0.1% potassium sorbate | |
| Days at ambient | No sonication | 1 minute sonication | No sonication | 1 minute sonication |
| 0 | 0.192 | 0.195 | 0.192 | 0.195 |
| 2 | 0.234 | 0.215 | 0.235 | 0.211 |
| 3 | 0.238 | 0.230 | 0.226 | 0.216 |
| 6 | 0.207 | 0.198 | 0.202 | 0.194 |

A sample of the complexed mometasone furoate monohydrate nanosuspension of Example 5 (1 g) was diluted with 0.9% saline solution or deionized water (9 g) and incubated in SNF at 37° C. at a concentration of approximately 0.2 mg/mL. The corresponding uncomplexed mometasone furoate monohydrate nanosuspension of Example 4 step 2 after the same dilution (1 g plus 9 g of saline (0.9% NaCl/deionized water (w/w)) or deionized water) was incubated side-by-side as a control for each curing time point. Two days after addition of the complexing agent, the D50 values of the complexed suspension with and without potassium sorbate were in the range of 3-11 microns after incubation in SNF at 37° C. At day 3, the D50 values dropped to 0.3-3 um range after SNF incubation. At day 6 of curing, the complexed mometasone suspensions exhibited D50 values <0.25 µm after incubation in SNF. The uncomplexed control suspension underwent complete flocculation after incubation in SNF with D50 values >18 µm at each time point (Table 5). The day 6 result of the complexed mometasone furoate monohydrate nanosuspension is also shown in Example 6 to further highlight its superior stability over the corresponding uncomplexed suspension when dispersed in SNF at 37° C.

TABLE 5

Table 5. D50 (D90) values (µm) of mometasone furoate monohydrate nanosuspensions in the presence of a complexing agent after incubation in SNF at 37° C. for 15 and 30 min at various curing time points (the corresponding uncomplexed suspension was incubated side-by-side as control for each curing time point).

| Mometasone furoate monohydrate suspension | Cured for 2 days* | | Cured for 3 days | | Cured for 6 days | |
|---|---|---|---|---|---|---|
| | After 15 min incubation | After 30 min incubation | After 15 min incubation | After 30 min incubation | After 15 min incubation | After 30 min incubation |
| Uncomplexed | 18.219 (55.701) | 29.84 (102.777) | 26.578 (86.334) | 38.582 (95.240) | 33.638 (86.741) | 39.996 (115.121) |
| Complexed | 11.236 (24.989) | 5.637 (12.427) | 3.111 (7.592) | 0.671 (5.060) | 0.257 (0.389) | 0.242 (0.404) |
| Complexed and preserved | 9.447 (20.456) | 3.268 (8.083) | 0.325 (13.448) | 0.326 (11.143) | 0.228 (0.369) | 0.23 (0.374) |

*Dilution was done with deionized water

It is totally unexpected that longer incubation in SNF of the complexed particles would get smaller over a longer incubation period.

Example 6

Figure 5:
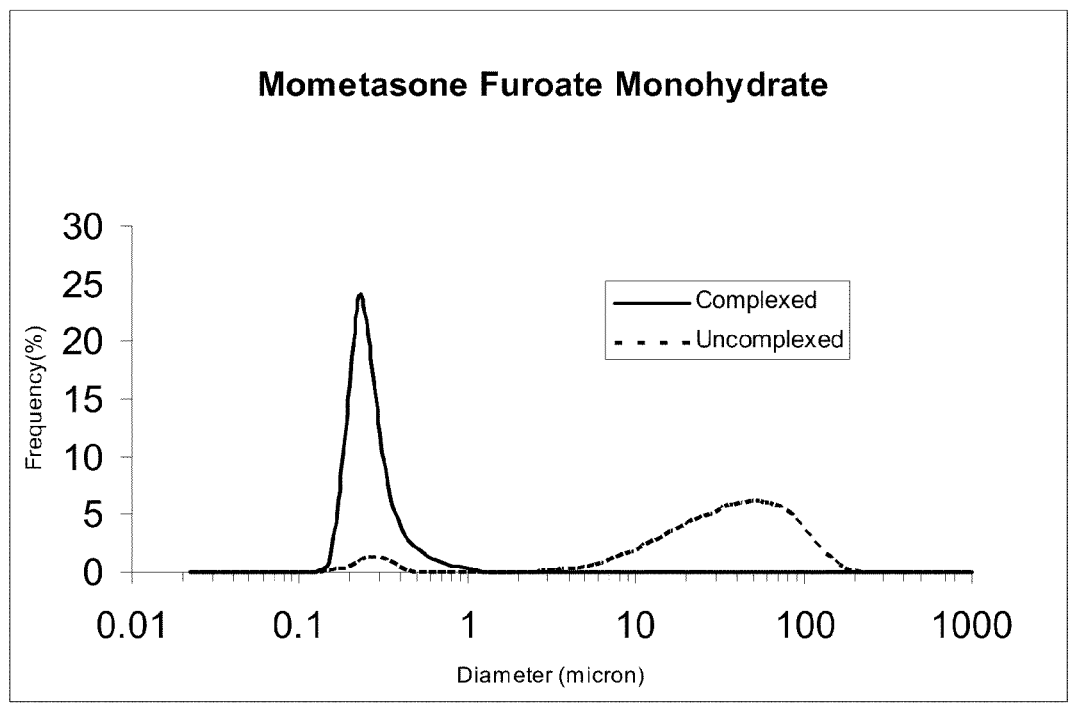
Figure 6:
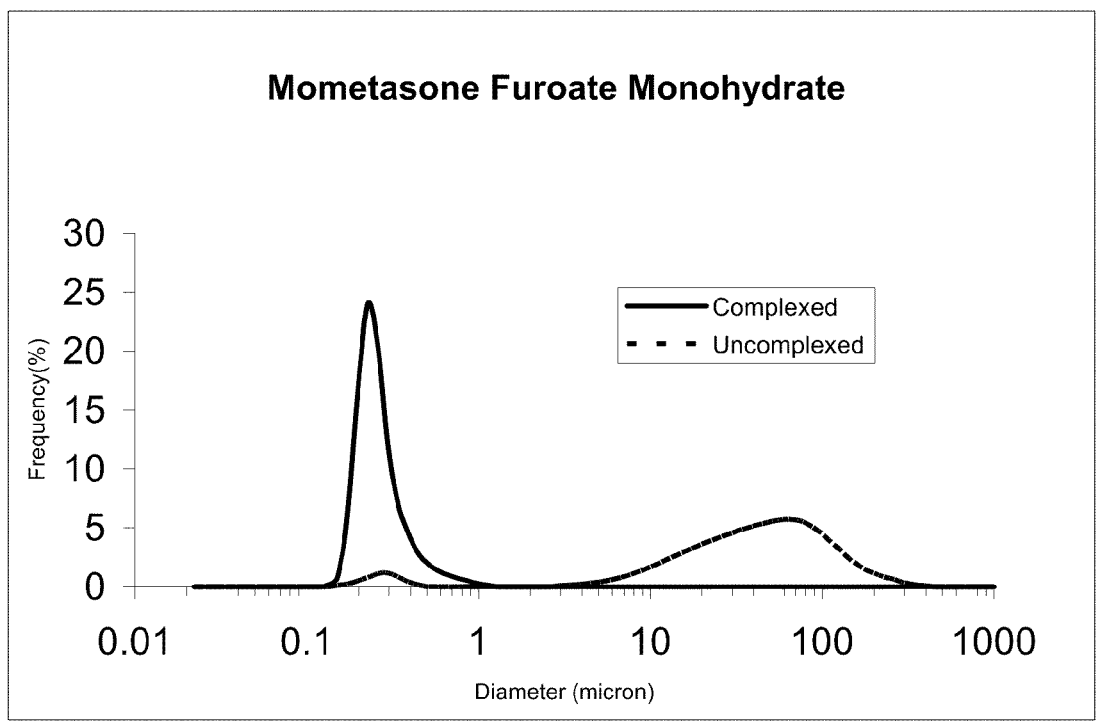

Complexed Dilute Mometasone Furoate Monohydrate (0.05% w/w) Nanoparticulate Suspensions Versus the Uncomplexed Suspension in SNF Sample of the complexed (with and without potassium sorbate as a preservative) mometasone furoate monohydrate nanosuspension of Example 5 cured for 6 days and uncomplexed nanosuspension of Example 4, 1 g each, were diluted separately with saline (0.9% NaCl/deionized water (w/w)) solution (0.9%) to obtain approximately 0.05% w/w complexed and uncomplexed mometasone furoate nanoparticulate suspensions. The mometasone nanosuspensions were incubated in SNF at 37° C. side-by-side at a concentration of approximately 0.2 mg/mL for an appropriate time. Particle size was measured. The particle size distribution curves of the complexed and uncomplexed mometasone furoate monohydrate nanosuspension after 15 and 30 min incubation in simulated nasal fluid are shown in FIG. 5 and FIG. 6 respectively. The D50 and D90 values before and after incubation are shown in Table 6.

TABLE 6

Table 6: D50 (D90) values (μm) of complexed and uncomplexed mometasone furoate monohydrate nanosuspensions before and after incubation in SNF at 37° C.

| Mometasone furoate monohydrate suspension | Initial* | After 15 min incubation in SNF | After 30 min incubation in SNF |
|---|---|---|---|
| Complexed | 207 (0.327) | 0.257 (0.389) | 0.242 (0.404) |
| Complexed and preserved | 202 (0.322) | 0.228 (0.369) | 0.230 (0.374) |
| Uncomplexed | 191 (0.310) | 33.638 (86.741) | 39.996 (115.121) |

*Initial D50 (D90) values are for concentrated stock suspensions

Example 7

Stability of 0.05% Complexed Mometasone Monohydrate Versus Uncomplexed Nanoparticulate Suspensions A. Formulation Preparation
1. Complexed Mometasone Furoate Monohydrate Nanoparticulate Formulation 0.05% w/w A sample of the complexed mometasone furoate monohydrate suspension of Example 5 (12.3 g) was mixed with deionized water (87.7 g) to obtain a pharmacologically relevant formulation containing 0.05% w/w of mometasone furoate (calculated on anhydrously basis), 0.05% HPMC, 0.001% sodium lauryl sulfate, 0.014% methylparaben sodium, 0.016% citric acid anhydrous and approximately 5 ppm of simethicone.
2. Uncomplexed Mometasone Furoate Monohydrate Nanoparticulate Formulation 0.05% w/w A sample of the uncomplexed mometasone furoate monohydrate suspension of Example 4 (12.3 g) was mixed with deionized water (87.7 g), to obtain a pharmacologically relevant formulation containing 0.05% w/w of mometasone furoate monohydrate, 0.05% HPMC, 0.001% sodium lauryl sulfate and approximately 5 ppm of simethicone.

B. Stability Results
Accelerated Stability

The stability data for the complexed mometasone furoate monohydrate nanoparticulate formulation is shown in FIG. 7. After an initial increase in D50 from 220 nm to about 280 nm in day 1, the D50 value of the suspension remained unchanged afterward. There was no change in appearance.

The uncomplexed formulation on the other hand flocculated after 1 day at 40° C./100% RH. The D50 changed from 0.191 μm to 38.137 μm.

Storage at Ambient Conditions

The complexed mometasone furoate monohydrate nanosuspension also showed superior stability at ambient storage conditions over the uncomplexed suspension (Table 6). The uncomplexed mometasone suspension underwent instant flocculation upon a 10-fold dilution in saline (0.9% NaCl/deionized water (w/w)) while the particle size of the complexed suspension remained unchanged. Although the uncomplexed suspension did not exhibit an instant increase in D50 value upon dilution with deionized water, the particles completely flocculated after 16 days at ambient storage. The complexed mometasone particles exhibited much smaller increases in D50 values in both water and saline (0.9% NaCl/deionized water (w/w)solutions during this period and remained stable afterward. Furthermore, visual inspections of the complexed mometasone formulations did not reveal any change in appearance. The preservative potassium sorbate was added to the complexed and uncomplexed formulations at approximately 0.1% level.

TABLE 6

Table 6: D50 (D90) (μm) values of mometasone furoate monohydrate nanosuspensions at ambient storage conditions.

| Formulation type | medium | Stock suspension[a] | Immediately after dilution | 16 days | 24 days | 31 days |
|---|---|---|---|---|---|---|
| Complexed | saline (0.9% NaCl/deionized water (w/w)) | 0.207 (0.322) | 0.220 (0.348) | 0.248 (0.441) | 0.265 (0.433) | 0.244 (0.407) |
| Complexed | deionized water | 0.207 (0.322) | NT | 0.265 (0.434) | 0.249 (0.376) | 0.250 (0.451) |
| Complexed, preserved | saline (0.9% NaCl/deionized water (w/w)) | 0.202 (0.313) | NT | 0.282 (1.499) | 0.288 (2.326) | 0.299 (1.513) |
| Uncomplexed, preserved[b] | saline (0.9% NaCl/deionized water (w/w)) | 0.191 (0.310) | 6.483 (29.684) | 15.921 (57.907) | NT | NT |
| Uncomplexed, preserved[b] | deionized water | 0.191 (0.310) | NT | 16.07 (160.050) | NT | NT |

NT: Not Tested
[a]The 0.05% w/w test lots were prepared by 10x dilution of the concentrated stock suspensions with either deionized water or 0.9% saline solution.
[b]Complete settlement after 16 days The purpose of this Example was to demonstrate superior storage stability of pharmacologically relevant complexed mometasone furoate monohydrate nanoparticulate formulations over the corresponding uncomplexed formulations under both ambient and accelerated conditions. This study also gave the surprising result that at lower concentrations of corticosteroids, accelerated curing at temperatures higher than ambient are needed to fully stabilize the composition. A 40° C. curing time of 24 hours was needed for these compositions at the 0.05% mometasone furoate monohydrate concentration to obtain a composition with stable storage and SNF dispersion characteristics.

Example 8

Storage Stability of Pharmacologically Relevant Complexed Mometasone Furoate Monohydrate Formulations over the Uncomplexed Mometasone Formulations with Additional HPMC added Post-Milling A. Mometasone Formulation Preparation
I. Complexed Mometasone Furoate Monohydrate Stock Suspension A sample of the uncomplexed mometasone furoate monohydrate nanoparticulate suspension of Example 4 (100 g) was mixed with a 10% w/w HPMC solution (4 g) containing 0.2% w/w sodium lauryl sulfate and approximately 40 ppm of 30% simethicone. The suspension was thoroughly mixed.

To a portion of the above suspension (100 g) was further added methylparaben sodium (113 mg), citric acid anhydrous (127 mg) and potassium sorbate (70 mg). The resultant suspension was thoroughly mixed and kept at ambient for particle size to cure.

II. Pharmacologically Relevant Complexed Mometasone Furoate Monohydrate 0.05% w/w Formulations A sample of the complexed mometasone furoate monohydrate stock suspension (4 g) was mixed with an appropriate diluent (27.2 g) (deionized water or saline (0.9% NaCl/deionized water (w/w)) and mixed thoroughly to obtain the 0.05% w/w mometasone formulations containing 0.097% HPMC, 0.002% sodium lauryl sulfate, 0.014% methylparaben sodium, 0.016% citric acid anhydrous, 0.009% potassium sorbate and approximately 0.5 ppm of 30% simethicone emulsion.

III. Pharmacologically Relevant Uncomplexed Mometasone Furoate Monohydrate 0.05% w/w Formulations To a sample of the uncomplexed mometasone furoate monohydrate nanoparticulate suspension (40 g) containing the additional HPMC as described above was added potassium sorbate (28 mg) and citric acid anhydrous (36 mg) to obtain the preserved uncomplexed mometasone furoate monohydrate stock suspension.

The uncomplexed monohydrate stock suspension (4 g) was mixed with an appropriate diluent (27.2 g) (deionized water or saline (0.9% NaCl/deionized water (w/w)) and mixed thoroughly to obtain the corresponding 0.05% w/w uncomplexed mometasone formulations having the same composition without the methylparaben sodium.

B. Stability Results

The stability results are shown in Table 7. The data has demonstrated superior storage stability of the complexed mometasone furoate monohydrate over the uncomplexed formulations under the same conditions. The uncomplexed mometasone furoate monohydrate formulation exhibited very poor stability upon dilution with saline (0.9% NaCl/deionized water (w/w)) solution at both ambient and accelerated storage conditions. Minor flocculation was observed after 14 hours at ambient and complete settlement at 40° C. After 4 days at ambient, this formulation completely flocculated with a D50 value of 17 µm. On the other hand, particle size of the complexed mometasone formulation remained essentially unchanged during this period at both ambient and accelerated conditions. In deionized water, the uncomplexed mometasone nanoparticles were more stable compared to saline (0.9% NaCl/deionized water (w/w)), these particles still exhibited significant increase in D50 values and complete flocculation occurred after 4 days at 40° C. D50 values of the complexed mometasone nanoparticles remained essentially unchanged under these conditions.

TABLE 7

Table 7: Stability data of complexed and uncomplexed mometasone furoate monohydrate nanosuspensions 0.05% w/w under both ambient and accelerated storage conditions

| Mometasone furoate monohydrate nanosuspension | Initial D50 (µm) before/after 1 min sonication | Initial D90 (µm) before/after 1 min sonication | 4 days at Ambient | | 4 days at 40° C./100% RH | |
|---|---|---|---|---|---|---|
| | | | D50 (µm) before/after 1 min sonication[a] | D90 (µm) before/after 1 min sonication[a] | D50 (µm) before/after 1 min sonication[a] | D90 (µm) before/after 1 min sonication[a] |
| Uncomplexed in deionized water | 0.235/0.210 | 0.833/0.382 | 0.280/0.214 | 1.774/0.342 | 0.296/0.228[c] | 2.594/0.429 |
| Complexed in deionized water | 0.236/0.217 | 0.375/0.339 | 0.235/0.225 | 0.381/0.368 | 0.237/0.215 | 0.392/0.338 |
| Uncomplexed in saline (0.9% NaCl/deionized water (w/w)) | 0.372/0.232 | 10.246/0.580 | 17.052/0.264[b] | 42.972/5.432 | 12.144/0.284[c] | 32.057/4.073 |
| Complexed in saline (0.9% NaCl/deionized water (w/w)) | 0.217/0.201 | 0.340/0.320 | 0.208/0.199 | 0.331/0.311 | 0.232/0.209 | 0.386/0.329 |

[a]Particle size measurements were taken after re-suspending all the precipitation by hand shaking.
[b]Minor flocculation observed after 14 hours and complete settlement after 4 days.
[c]Complete settlement after 14 hours Example 8 demonstrated that ambient curing is possible for about 0.05% mometasone Furoate monohydrate suspensions if the amount of the non-ionic stabilizer (HPMC) was increased to about 0.1% w/w of the suspension.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A pharmaceutical formulation of stabilized corticosteroid particles, comprising a corticosteroid, a hydrophilic polymer, a wetting agent selected from the group consisting of sodium lauryl sulfate, a pharmaceutically acceptable salt of docusate, Tween 20, Tween 80 and mixtures thereof, and an effective amount of a complexing agent that stabilizes particle growth after an initial particle growth and endpoint is reached, the complexing agent consisting of at least one paraben or a pharmaceutically acceptable salt thereof, wherein the stabilized particles have a volume weighted median diameter (D50) of the particles from about 50 nm to about 500 nm, and wherein said pharmaceutical formulation is suitable for administration intranasally or via inhalation.

2. The pharmaceutical formulation of claim 1, which is in the form of an aqueous dispersion containing the particles in from about 0.1% to about 0.9% saline.

3. The pharmaceutical formulation of claim 1 suitable for inhalation administration, consisting of the particles suspended in a nebulizing media.

4. The pharmaceutical formulation of claim 1, suitable for inhalation administration, consisting of the particles in dry form.

5. The pharmaceutical formulation of claim 1, wherein the complexing agent is present in an amount from about 0.005 to about 40% w/w, based on the weight of the particles.

6. The pharmaceutical formulation of claim 1, wherein the at least one paraben is selected from the group consisting of methylparaben, ethylparaben, propylparaben, pharmaceutically acceptable salts thereof and mixtures thereof.

7. The pharmaceutical formulation of claim 1, wherein the hydrophilic polymer is selected from the group consisting of a cellulosic polymer, a vinyl polymer and mixtures thereof.

8. The pharmaceutical formulation of claim 1, wherein the hydrophilic polymer comprises a cellulosic polymer.

9. The pharmaceutical formulation of claim 1, wherein the hydrophilic polymer is a cellulose ether.

10. The pharmaceutical formulation of claim 1, wherein the hydrophilic polymer is hydroxypropylmethylcellulose.

11. The pharmaceutical formulation of claim 1, wherein the hydrophilic polymer is a vinyl polymer.

12. The pharmaceutical formulation of claim 1, wherein the hydrophilic polymer is a polyvinyl alcohol.

13. The pharmaceutical formulation of claim 1, wherein the corticosteroid is selected from the group consisting of budesonide, triamcinolone acetonide, triamcinolone, mometasone, mometasone furoate anhydrous, flunisolide, fluticasone propionate, fluticasone, beclomethasone dipropionate, dexamethasone, triamincinolone, beclomethasone, fluocinolone, fluocinonide, flunisolide hemihydrate, mometasone furoate monohydrate, clobetasol, and pharmaceutically acceptable salts, hydrates, polymorphs and combinations thereof.

14. The pharmaceutical formulation of claim 1, wherein the corticosteroid is selected from the group consisting of mometasone, mometasone furoate anhydrous, mometasone furoate monohydrate and pharmaceutically acceptable salts, hydrates, polymorphs and combinations thereof.

15. The pharmaceutical formulation of claim 1, wherein a single dose of intranasal suspension provides a therapeutically effective amount of the corticosteroid that is about ⅓ to about ½ the dose required to achieve therapeutic efficacy as compared to an intranasal suspension with particle size >1 micron containing the same corticosteroid.

16. Complexed stabilized corticosteroid particles, comprising particles of a corticosteroid together with an effective amount of a complexing agent that stabilizes particle growth, the complexing agent consisting of at least one paraben or a pharmaceutically acceptable salt thereof, a hydrophilic polymer, and a wetting agent selected from the group consisting of sodium lauryl sulfate, a pharmaceutically acceptable salt of docusate, Tween 20, Tween 80 and mixtures thereof, wherein the stabilized particles have a volume weighted median diameter (D50) of the particles from about 50 nm to about 500 nm, and wherein said particles are suitable for administration intranasally or via inhalation.

17. The complexed stabilized corticosteroid particles of claim 16, wherein the at least one paraben is selected from the group consisting of methylparaben, ethylparaben, propylparaben, pharmaceutically acceptable salts thereof and mixtures thereof.

18. The complexed stabilized corticosteroid particles of claim 16, suitable for inhalation administration, consisting of the particles suspended in a nebulizing media.

19. The complexed stabilized corticosteroid particles of claim 16, suitable for inhalation administration, consisting of the particles in dry form.

20. The complexed stabilized corticosteroid particles of claim 16, wherein the complexing agent is present in an amount from about 0.005 to about 40% w/w, based on the weight of the particles.

21. The complexed stabilized corticosteroid particles of claim 16, wherein the corticosteroid is selected from the group consisting of budesonide, triamcinolone acetonide, triamcinolone, mometasone, mometasone furoate anhydrous, flunisolide, fluticasone propionate, fluticasone, beclomethasone dipropionate, dexamethasone, triamincinolone, beclomethasone, fluocinolone, fluocinonide, flunisolide hemihydrate, mometasone furoate monohydrate, clobetasol, and pharmaceutically acceptable salts, hydrates, polymorphs and combinations thereof.

22. The complexed stabilized corticosteroid particles of claim 16, wherein the corticosteroid is mometasone, mometasone furoate anhydrous, mometasone furoate monohydrate and pharmaceutically acceptable salts, hydrates, polymorphs and combinations thereof.

23. An aqueous nanosuspension of complexed stabilized corticosteroid particles, comprising complexed stabilized particles of a corticosteroid together with an effective amount of a complexing agent that stabilizes particle growth, a hydrophilic polymer, and a wetting agent, the complexing agent consisting of at least one paraben or a pharmaceutically acceptable salt thereof, the group consisting of sodium lauryl sulfate, a pharmaceutically acceptable salt of docusate, Tween 20, Tween 80 and mixtures thereof, wherein the complexed stabilized corticosteroid particles have a volume weighted median diameter (D50) of the particles from about 50 nm to about 500 nm, and wherein said nanosuspension is suitable for intranasal administration, the nanosuspension further comprising one or more excipients sleeted from the group consisting of a suspending agent, a humectant, a buffer, a surfactant, an antimicrobial preservative, and mixtures of any of the foregoing.

24. The aqueous nanosuspension of claim 23, wherein the complexed stabilized corticosteroid particles are suspended in from about 0.1% to about 0.9% saline.

25. The aqueous nanosuspension of claim 24, further comprising an effective amount of an antimicrobial preservative.

26. The aqueous nanosuspension of claim 23, wherein the at least one paraben is selected from the group consisting of methylparaben, ethylparaben, propylparaben, pharmaceutically acceptable salts thereof and mixtures thereof.

27. The pharmaceutical formulation of claim 1, further comprising benzoic acid, phenol, methyl anthranilate, pharmaceutically acceptable salts thereof, or mixtures thereof.

28. The complexed stabilized corticosteroid particles of claim 16, further comprising phenol, benzoic acid, methyl anthranilate, pharmaceutically acceptable salts thereof, or mixtures thereof.

* * * * *